US012569375B2

(12) United States Patent
Mizumoto

(10) Patent No.: US 12,569,375 B2
(45) Date of Patent: Mar. 10, 2026

(54) BOXER-SHORTS-TYPE DISPOSABLE DIAPER AND METHOD FOR PRODUCING SAME

(71) Applicant: DAIO PAPER CORPORATION, Shikokuchuo (JP)

(72) Inventor: Yousei Mizumoto, Tochigi (JP)

(73) Assignee: Daio Paper Corporation, Ehime (JP)

( * ) Notice: Subject to any disclaimer, the term of this patent is extended or adjusted under 35 U.S.C. 154(b) by 484 days.

(21) Appl. No.: 18/006,837

(22) PCT Filed: May 25, 2021

(86) PCT No.: PCT/JP2021/019766

§ 371 (c)(1),
(2) Date: Jan. 25, 2023

(87) PCT Pub. No.: WO2022/070502

PCT Pub. Date: Apr. 7, 2022

(65) Prior Publication Data

US 2023/0270602 A1      Aug. 31, 2023

(30) Foreign Application Priority Data

Sep. 30, 2020      (JP) ................................. 2020-164274

(51) Int. Cl.
A61F 13/15        (2006.01)
A61F 13/49        (2006.01)

(52) U.S. Cl.
CPC .... A61F 13/4902 (2013.01); A61F 13/15577 (2013.01); *A61F 2013/49034* (2013.01); *A61F 2013/49092* (2013.01)

(58) Field of Classification Search
CPC ............ A61F 13/4902; A61F 13/15577; A61F 13/494; A61F 13/15593; A61F 13/15804;
(Continued)

(56) References Cited

U.S. PATENT DOCUMENTS 7,875,014 B2 *   1/2011   Hendren ............... A61F 13/565
                                                              604/396
2003/0217803 A1 *  11/2003  Hermansson ..... A61F 13/15747
                                                              156/204
(Continued)

FOREIGN PATENT DOCUMENTS

EP            1875819           8/2010
JP        2002530153 A         9/2002
(Continued)

OTHER PUBLICATIONS

International Search Report for PCT/JP2021/019766, dated Aug. 17, 2021.

*Primary Examiner* — Jacqueline F Stephens
(74) *Attorney, Agent, or Firm* — Andrus Intellectual Property Law, LLP

(57)          ABSTRACT

Provided are disposable diapers that are easy to manufacture. This problem is solved by a boxer-shorts-type disposable diaper including an outer member having ventral and dorsal outer members and a crotch outer member extending therebetween and to be placed through the crotch of a wearer, and an inner member containing an absorber body and joined to the interior face of at least the crotch outer member, wherein the ventral/dorsal outer members are joined in the middle of the width direction in the crotch-side end to the crotch outer member to form ventral/dorsal seams, respectively, the areas extending along the edges of the leg openings in the ventral/dorsal outer members are stretchable in the width direction, and the areas extending along the edges of the leg openings in the crotch outer member are stretchable in the front-back direction.

5 Claims, 15 Drawing Sheets

(58) Field of Classification Search
CPC .......... A61F 13/49012; A61F 13/49017; A61F
13/496; A61F 2013/49034; A61F
2013/49092
See application file for complete search history.

(56) References Cited

U.S. PATENT DOCUMENTS

| | | | |
|---|---|---|---|
| 2004/0098791 A1* | 5/2004 | Faulks .............. | A61F 13/15699 |
| | | | 2/400 |
| 2004/0108054 A1 | 6/2004 | Otsubo et al. | |
| 2004/0116881 A1* | 6/2004 | Nordness ............. | A61F 13/496 |
| | | | 604/358 |
| 2006/0243378 A1* | 11/2006 | Alberts ............. | A61F 13/15739 |
| | | | 156/204 |
| 2009/0312739 A1 | 12/2009 | Umebayahi et al. | |
| 2013/0281958 A1 | 10/2013 | Bäck et al. | |

FOREIGN PATENT DOCUMENTS

| | | | | |
|---|---|---|---|---|
| JP | 2003339769 A | 12/2003 | | |
| JP | 2009106666 A | 5/2009 | | |
| JP | 4912199 B2 | 4/2012 | | |
| JP | 5717660 B2 | 5/2015 | | |
| JP | 6323379 B2 | 5/2018 | | |
| JP | 2019118557 A | 7/2019 | | |
| JP | 6752696 B2 | 9/2020 | | |
| WO | WO-2004075801 A1 * | 9/2004 | .............. | A41B 9/04 |

* cited by examiner

[FIG.1]
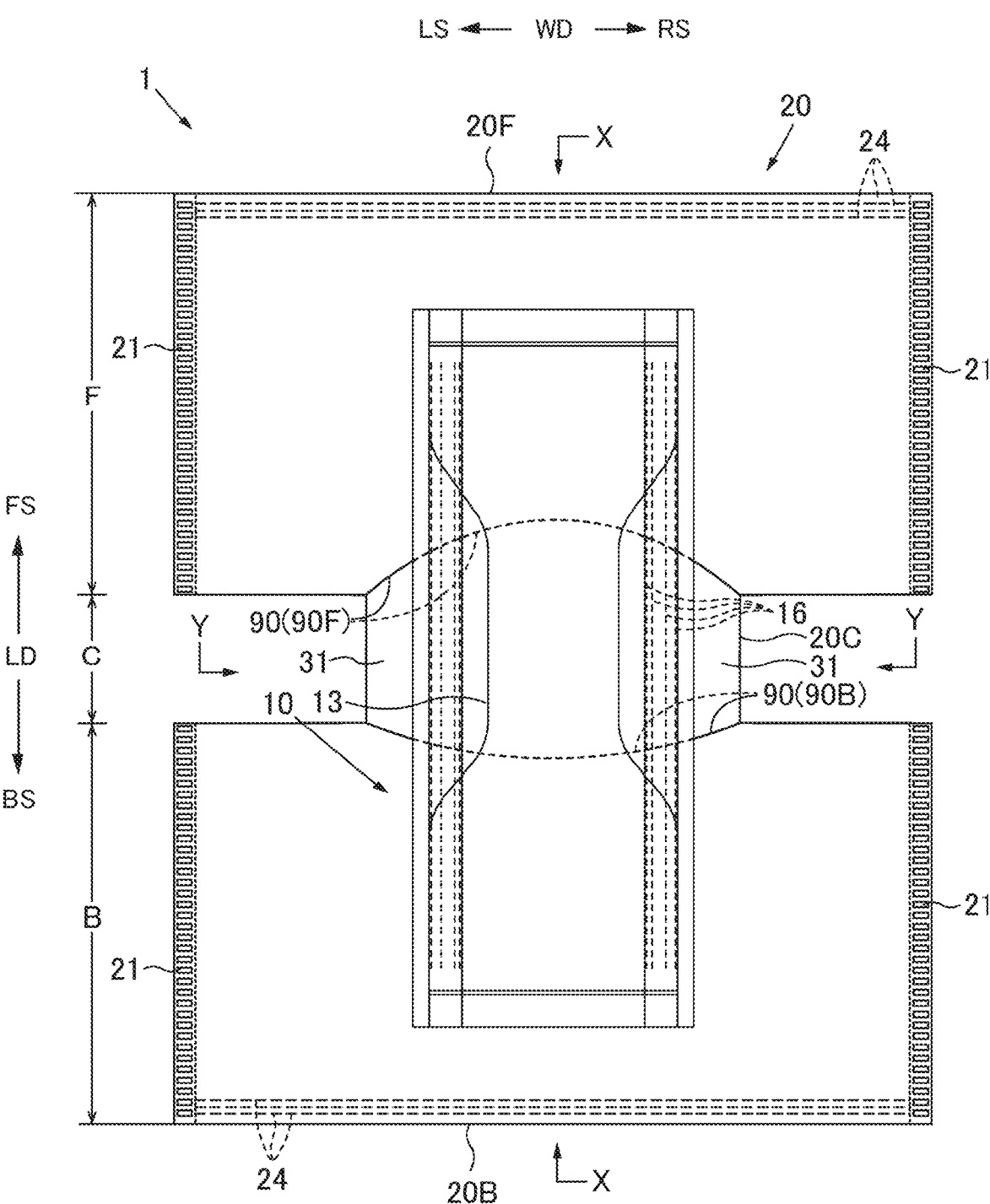

[FIG.2]
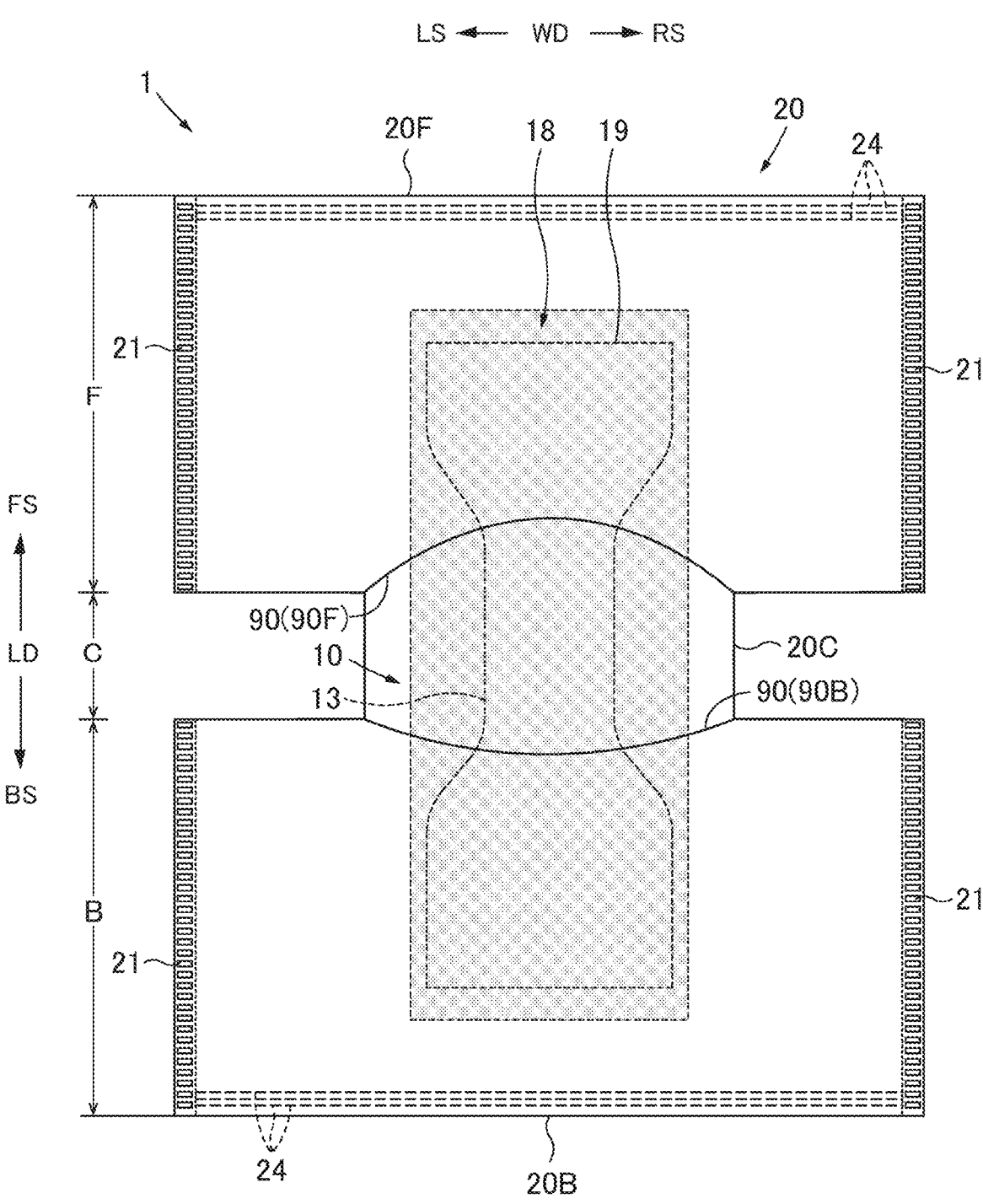

[FIG.3]
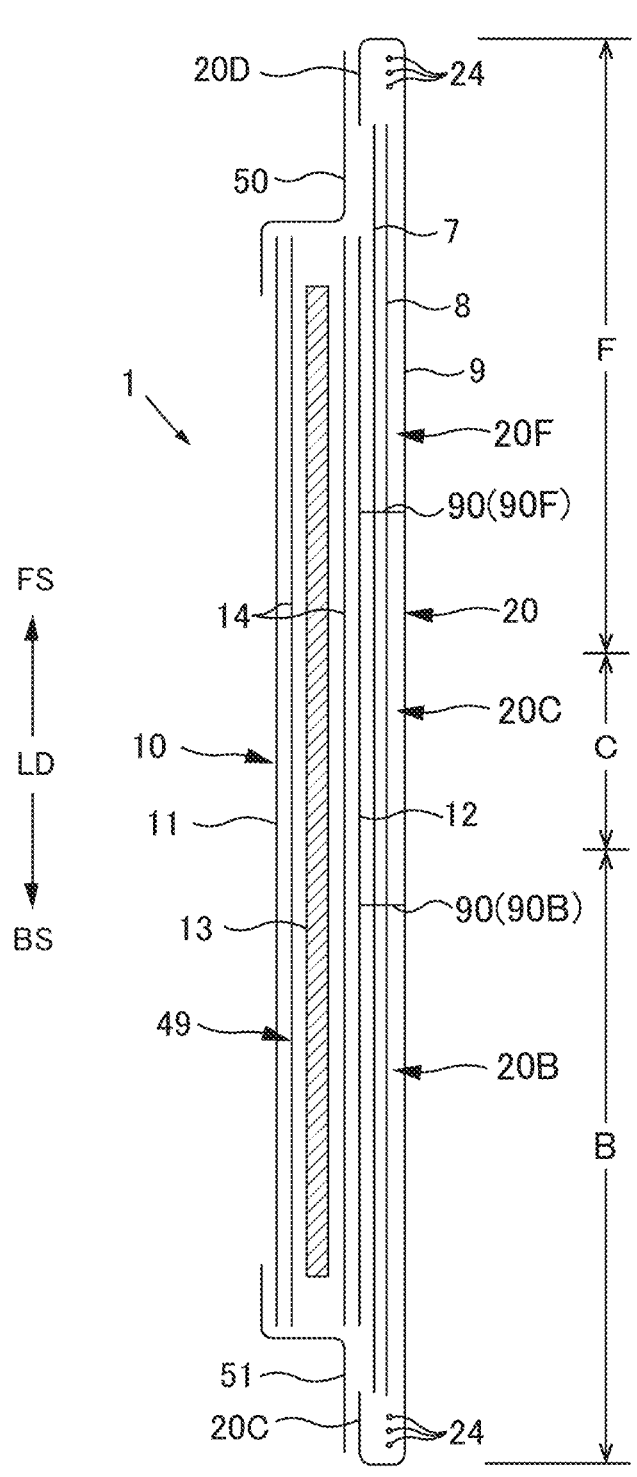

[FIG.4]
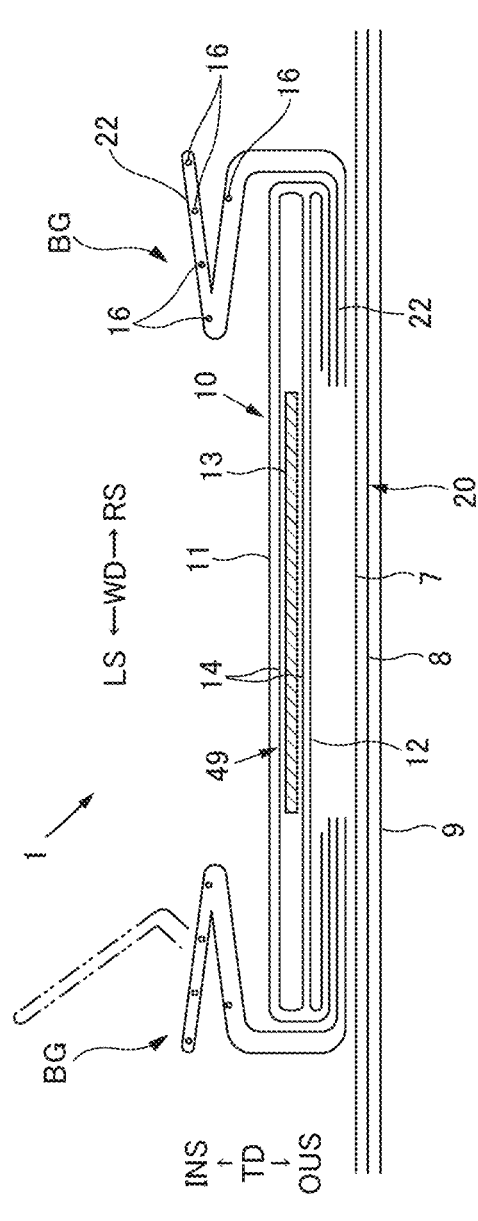

[FIG.5]
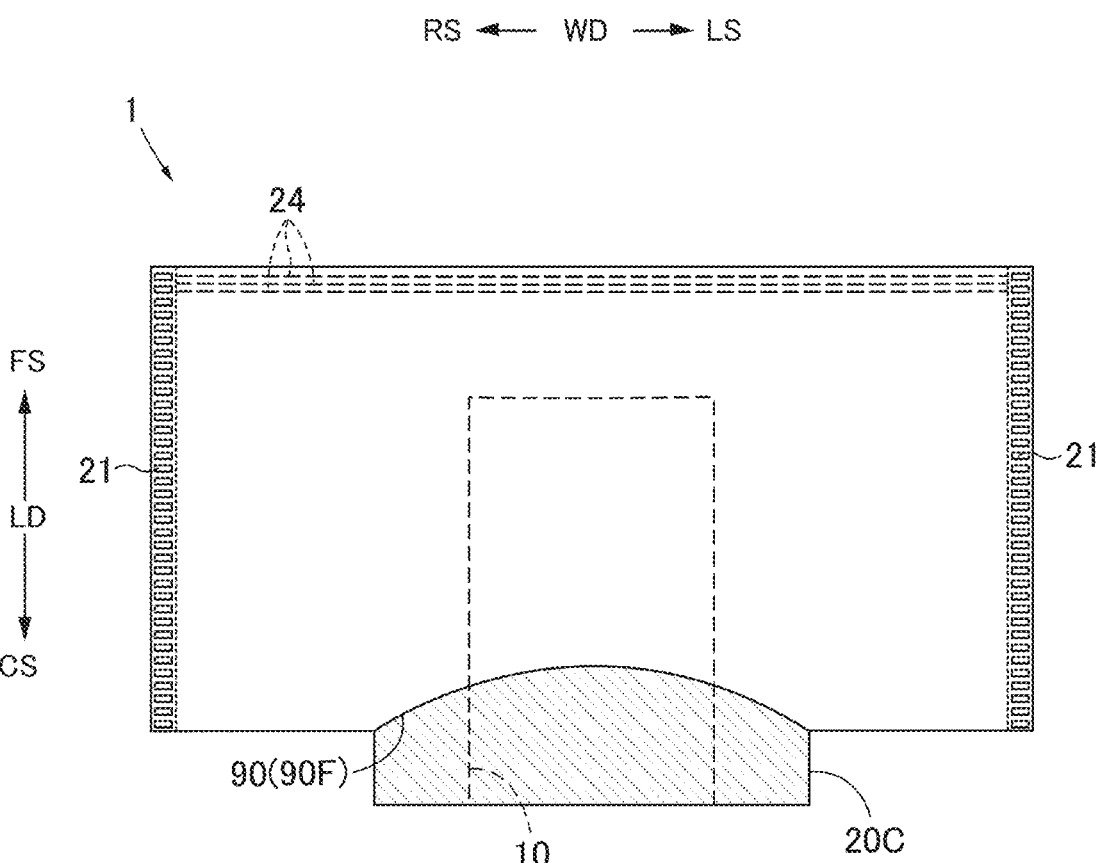

[FIG.6]
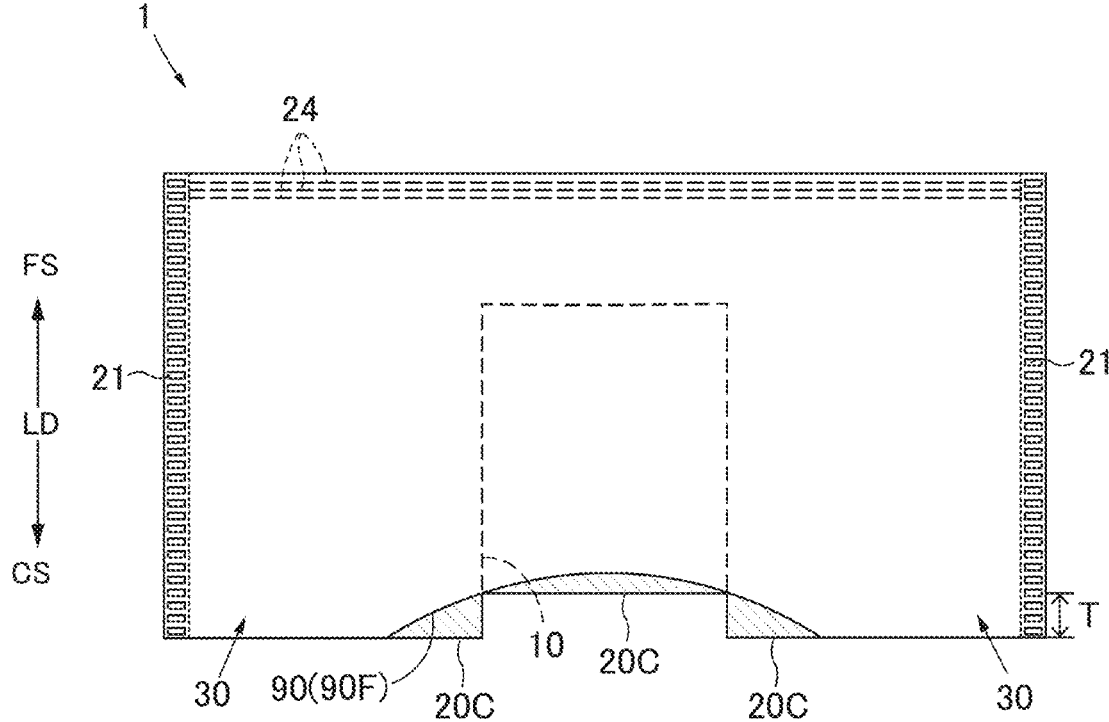

[FIG.7]
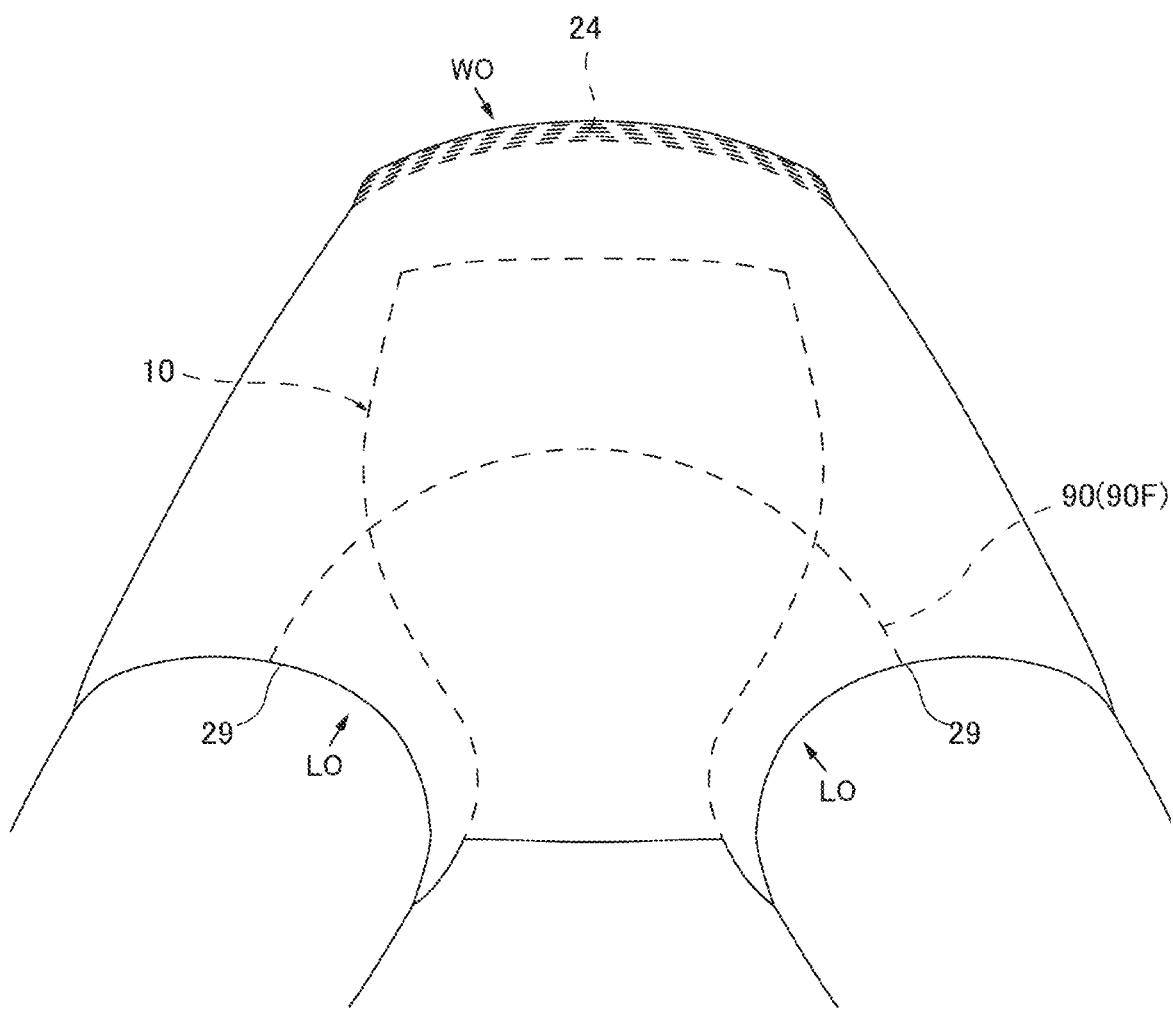

[FIG.8]
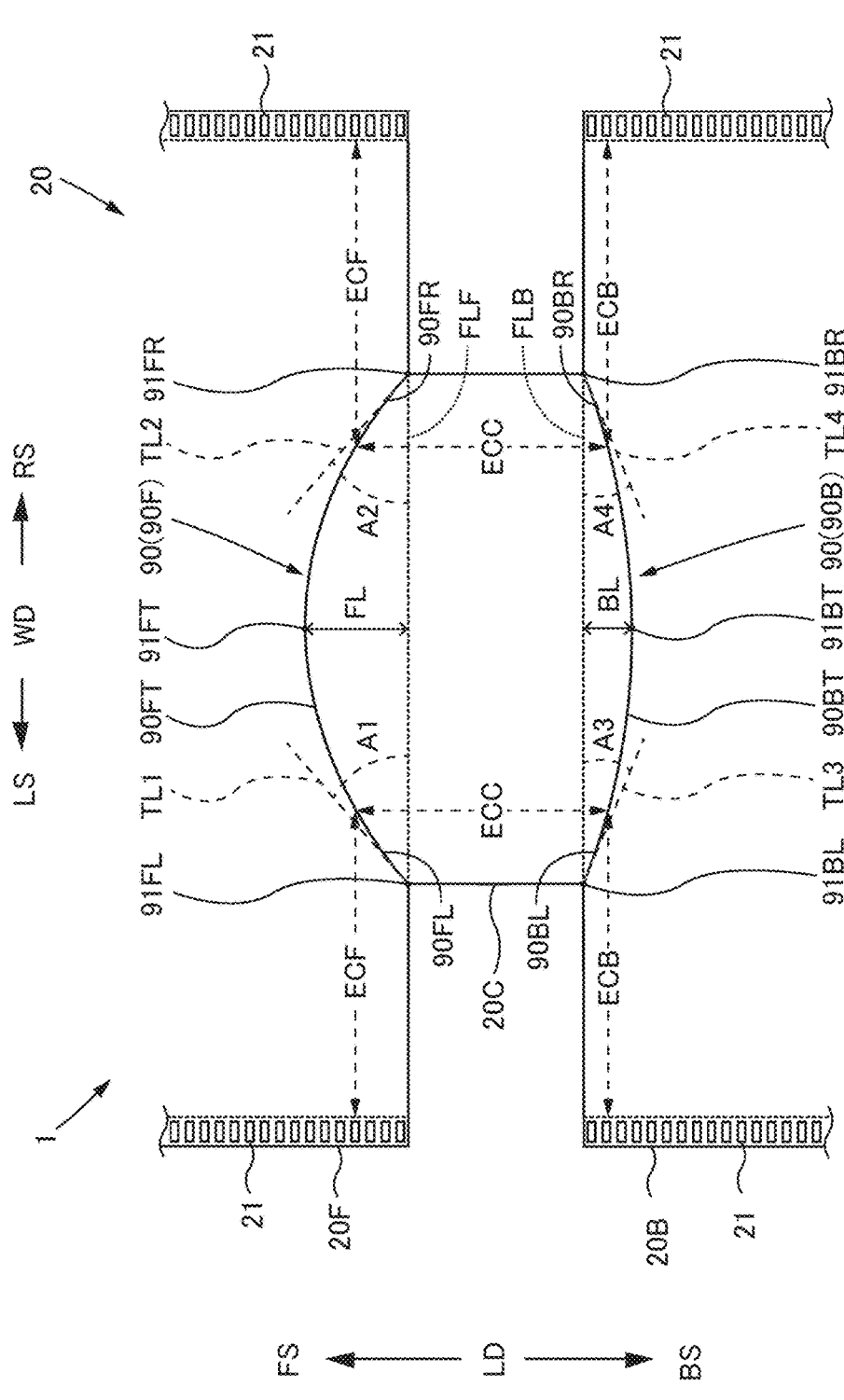

[FIG.9]
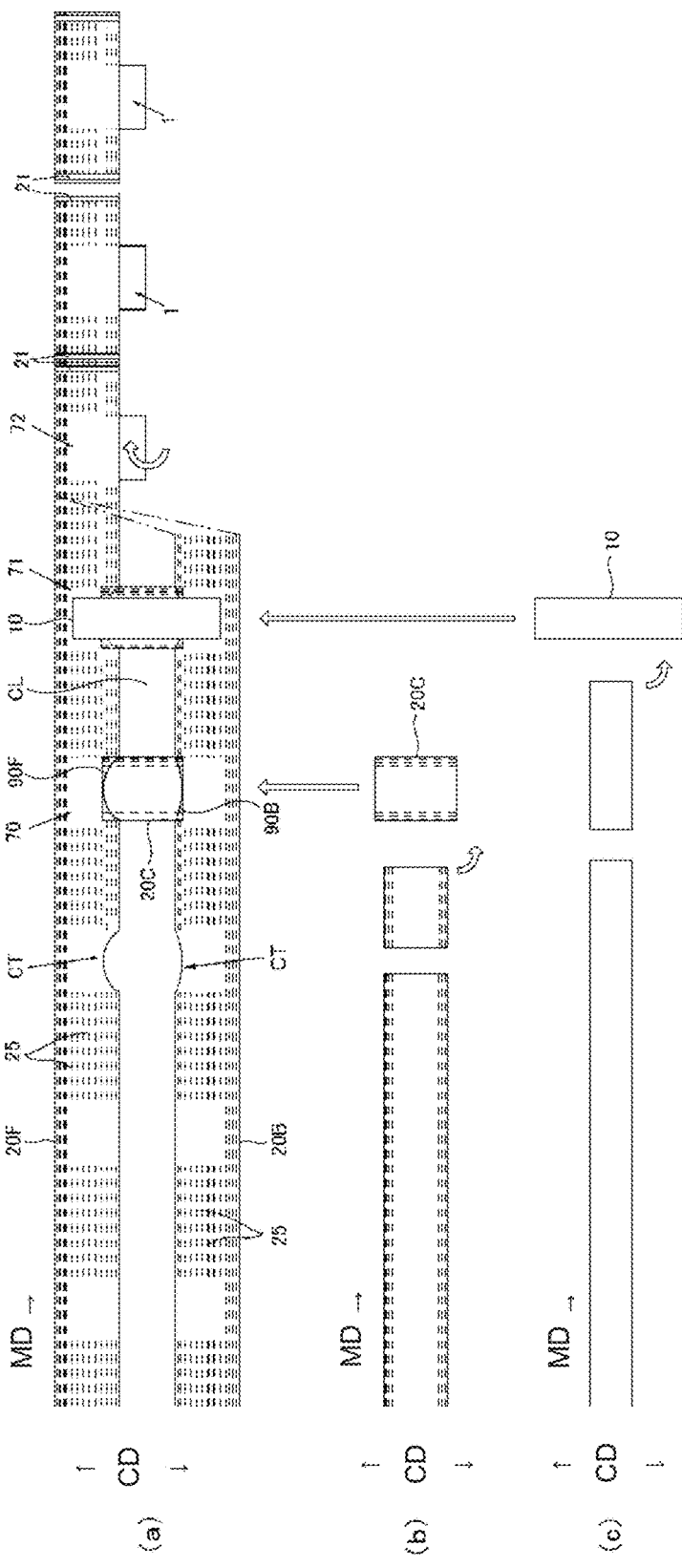

[FIG.10]
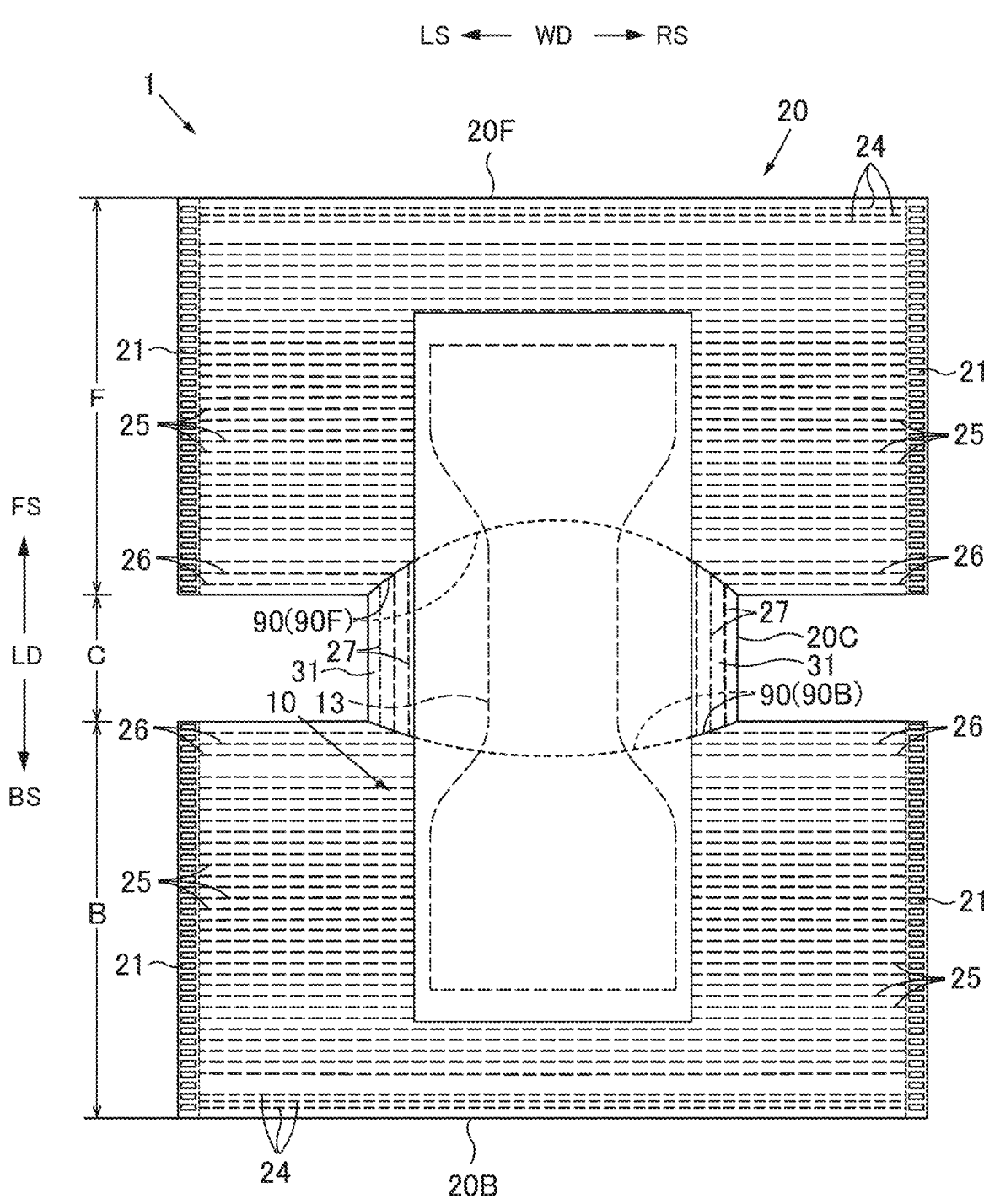

[FIG.11]
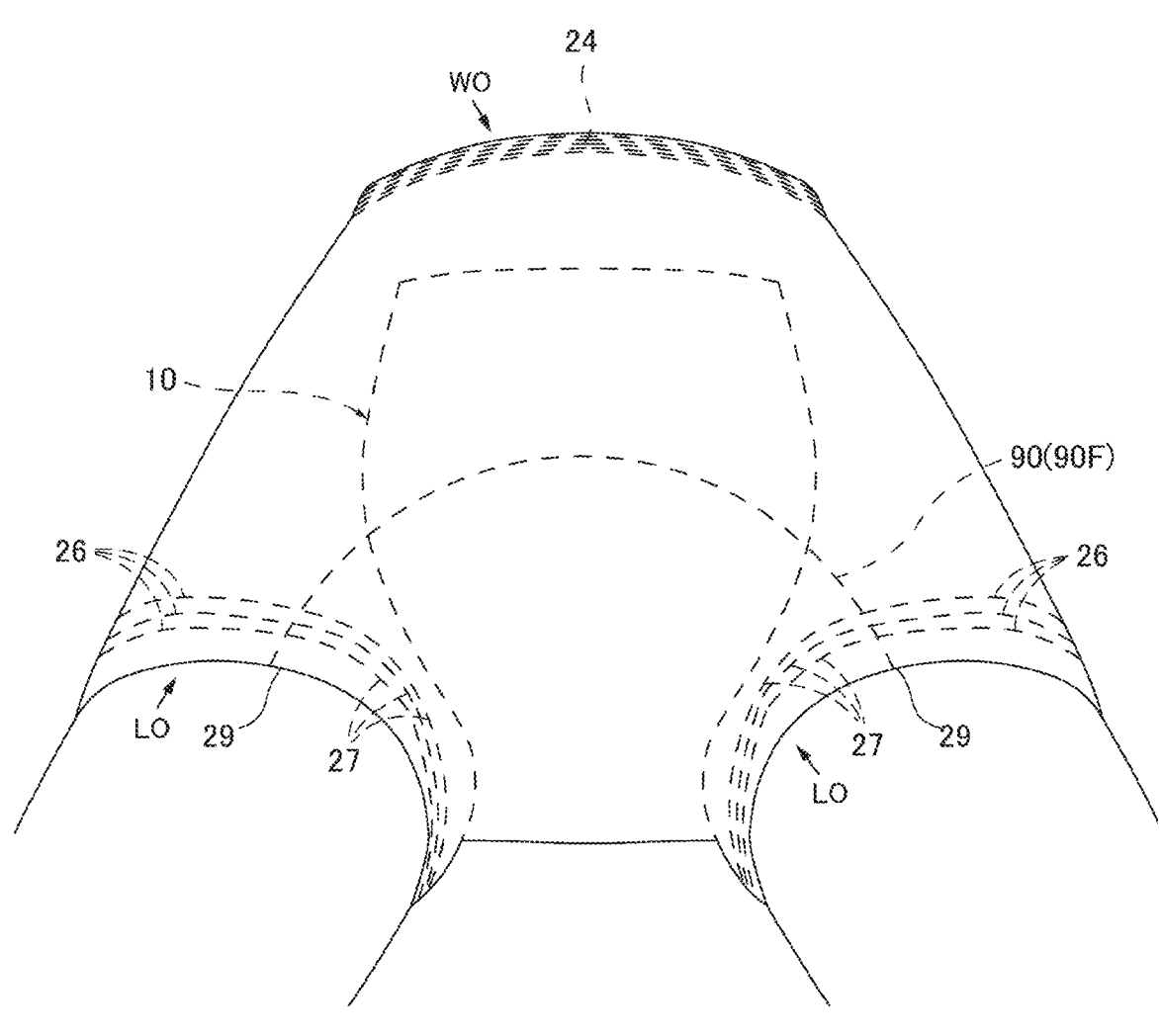

[FIG.12]
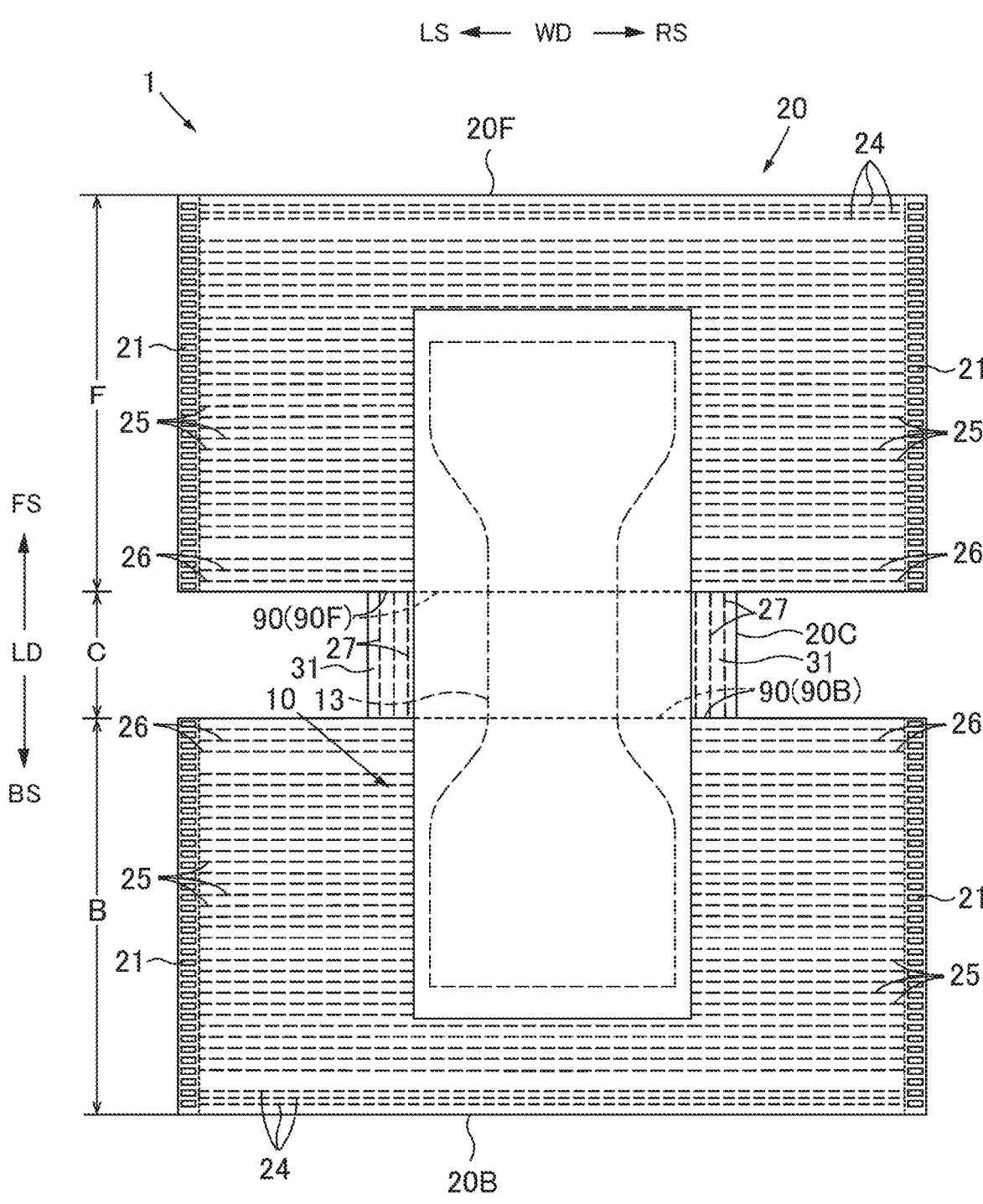

[FIG.13]
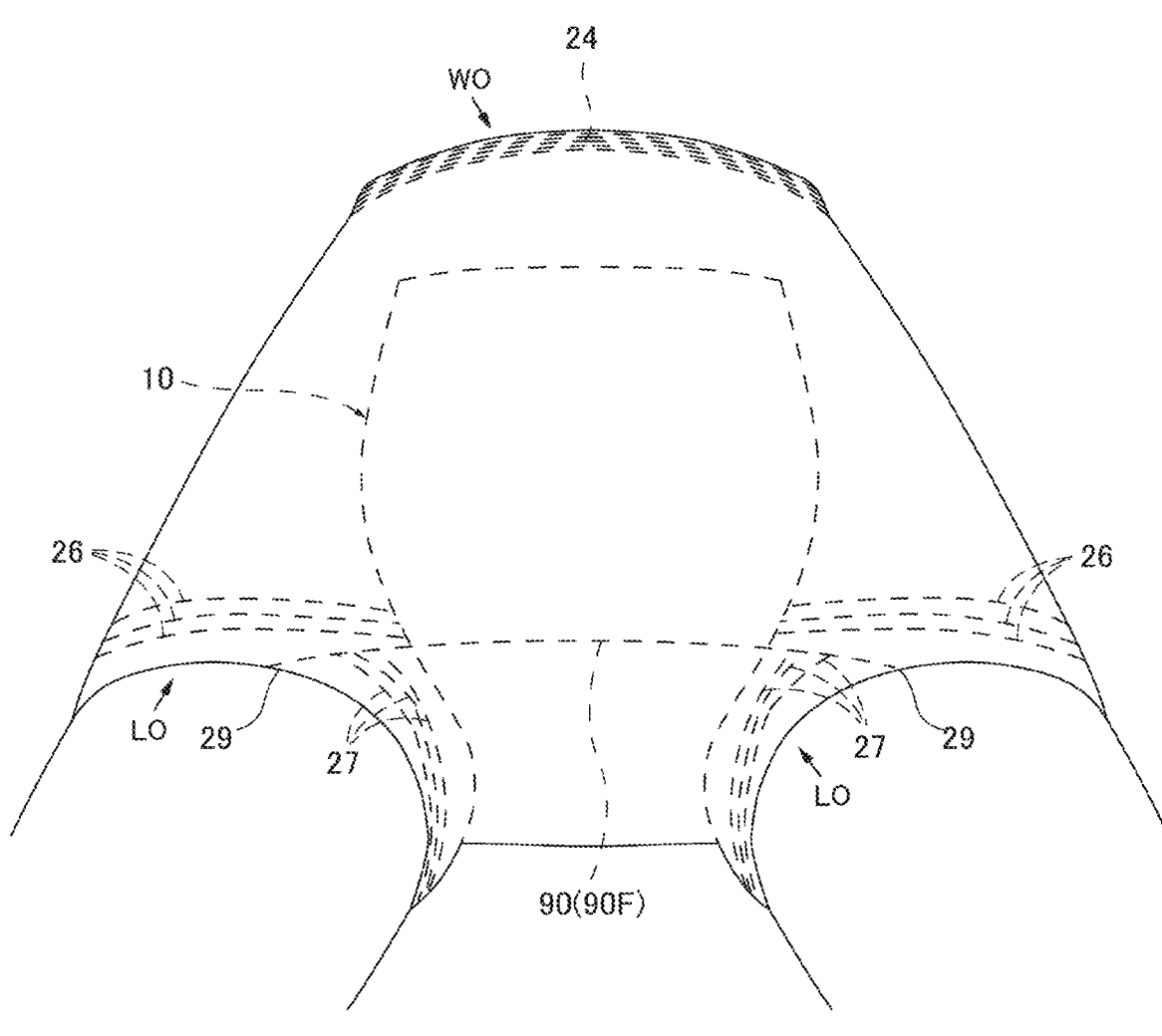

[FIG.14]
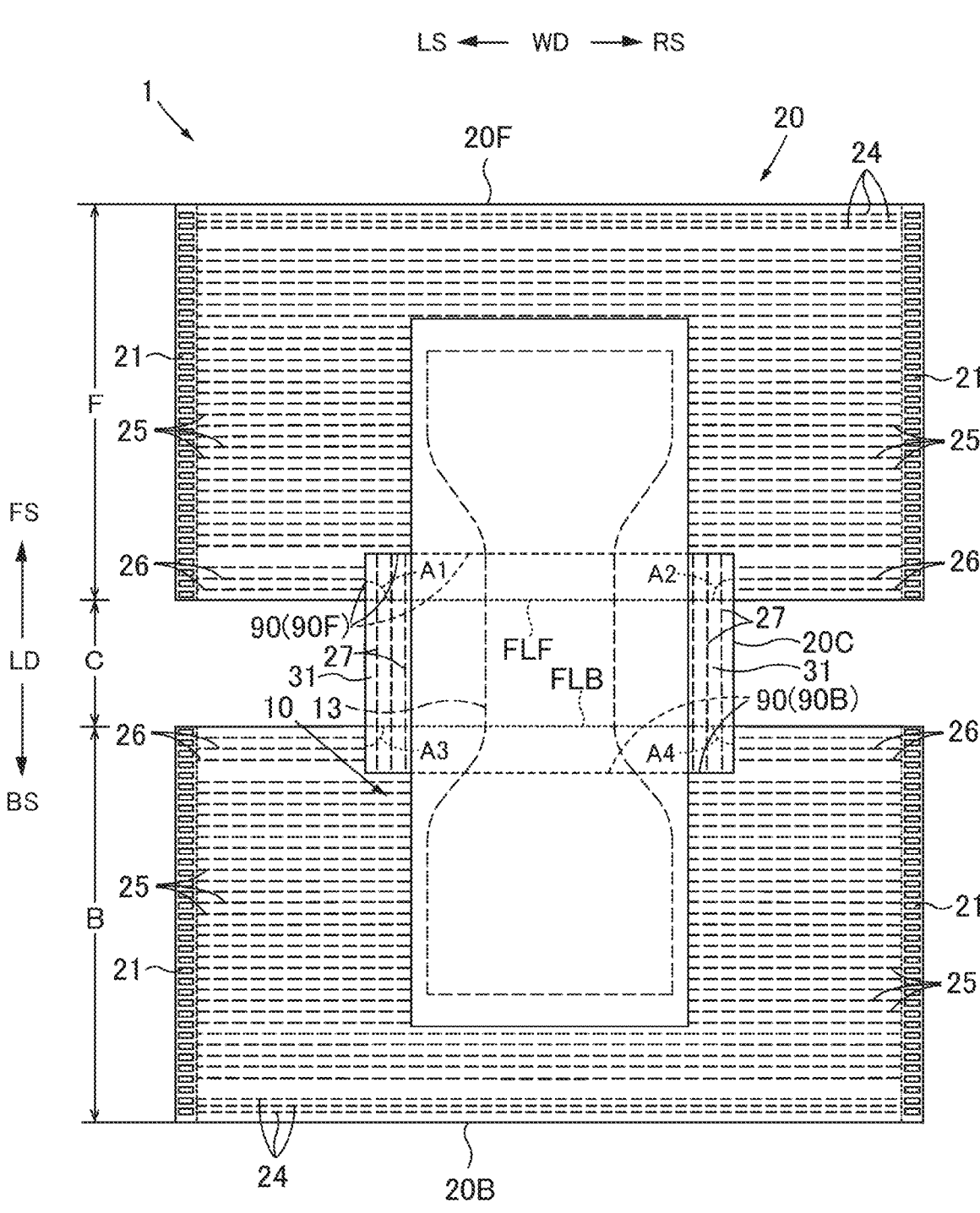

[FIG.15]
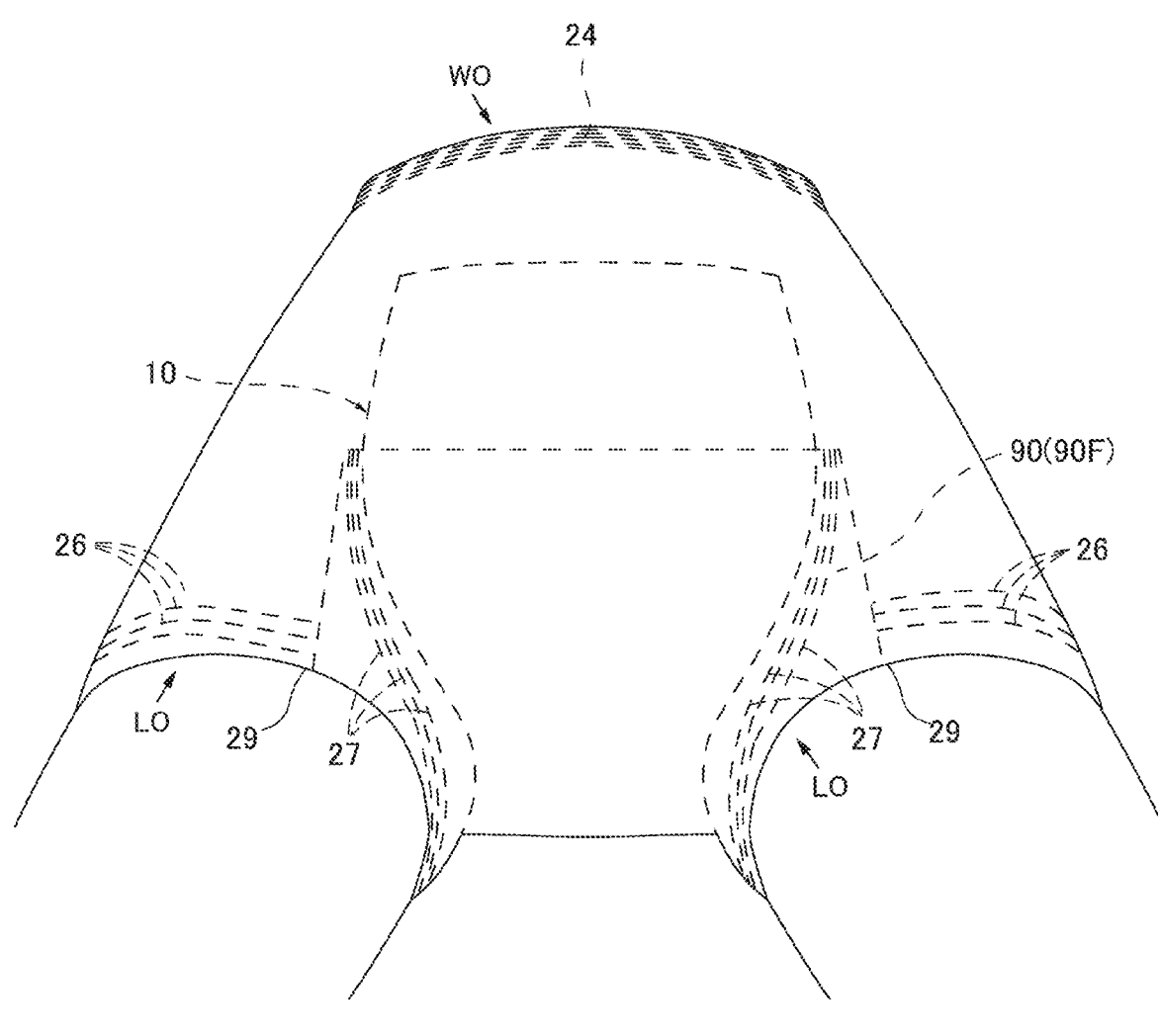

BOXER-SHORTS-TYPE DISPOSABLE DIAPER AND METHOD FOR PRODUCING SAME

CROSS-REFERENCE TO RELATED APPLICATIONS

This application is the U.S. national stage application of International Application PCT/JP2021/019766, filed May 25, 2021, which international application was published on Apr. 7, 2022, as International Publication WO 2022/070502 in the Japanese language. The International Application claims priority of Japanese Patent Application No. 2020-164274, filed Sep. 30, 2020. The international application and Japanese application are both incorporated herein by reference, in entirety.

FIELD OF ART

The present invention relates to boxer-shorts-type disposable diapers and a method for producing the same.

BACKGROUND ART

Conventionally known disposable diapers may generally be divided into two types, a tape type and an underpants type. In tape-type disposable diapers, the front body and the back body are connected to each other by means of tapes provided at the opposed lateral sides of the front or back body, to thereby form the lower-torso section for covering the lower torso of the wearer. At the same time, a waist opening and a pair of round-thigh openings are formed.

On the other hand, in underpants-type disposable diapers, the front body section and the back body section are joined to each other in advance along the opposed lateral sides by means of hot melt adhesives or the like, so that it forms the shape of an underpants without assembling like the tape-type disposable diapers.

The underpants-type disposable diapers include a briefs type, wherein round-groin edges are formed in a V-shape from below the crotch toward the lateral sides of the waist, and a boxer-shorts type, wherein round-thigh cylinders are formed for wrapping around the thighs.

The boxer-shorts-type disposable diapers, which have the round-thigh cylinders, have the advantages in that bodily waste is hard to leak through the leg openings, and are growing in demand with recent diversification of preferences in design. In particular, not a little consumers who used to wear boxer-shorts-type underwear, considering wearing disposable diapers as they experience remarkable incontinence symptoms at an advanced age (in and after their sixties), seek for wearing comfort and appearance comparable to those of the boxer-shorts-type underwear, and the boxer-shorts-type disposable diapers have good appeal to such consumers.

Boxer-shorts-type disposable diapers are proposed in prior art Patent Publications 1 to 4 to be mentioned below.

The disposable diaper disclosed in Patent Publication 1 includes a waist opening, a pair of leg openings, a pair of downwardly-extending leg sections extending downward along the legs of the wearer when worn to form the corresponding leg openings, at least a pair of leak proof walls each extending longitudinally and having a free end, a fixed end, and a free end portion containing the corresponding free end, and a pair of round-leg sheets having stretchability and each located laterally outward of the corresponding leak proof wall, wherein each leak proof wall has a free-endportion elastic member, which is an elastic member attached in its stretched state to the free end portion and extending in the longitudinal direction, wherein the transversely inner edge of each round-leg sheet is joined to between the free end and the fixed end of the leak proof wall, with each round-leg sheet in its non-stretched state. This publication discloses an advantage that, with such a structure, when a wearer puts on a diaper, the leg openings are oriented to the directions for passing the legs of the wearer, and are not narrowed, so that the legs are hardly caught on the edge of the leg openings when the wearer passes his legs through the leg openings, which facilitates insertion of the legs through the leg openings.

The boxer-shorts-type disposable diaper disclosed in Patent Publication 2 includes an outer member having a front body section, a back body section, a crotch section, and a pair of right and left round-leg covering sections forming a pair of right and left leg openings laterally outward in the width direction of the crotch section, and an absorbent body disposed in the crotch section inside the outer member, wherein in the inner thigh area on the inner perimeter of each of the pair of right and left round-leg covering sections is provided an inner thigh member, and the circumferential length of the end of each inner thigh member located on the leg-opening side is longer than the circumferential length of the other end of the inner thigh member. This publication discloses an advantage that the inner thigh members absorb the body fluid leaking out of the crotch along the inner thighs to prevent body fluid from leaking out of the leg openings, and keep the round-leg stretchable members, such as rubber threads, from directly contacting the skin.

The underpants-type disposable diaper disclosed in Patent Publication 3 has the front body section and the back body section joined along the opposed lateral sides and in the crotch area to form a waist opening and a pair of leg openings, wherein each of the front and back body sections is dented in approximately the middle of the edge located opposite to the waist opening edge, wherein the distance between the bottom of the dent and the waist opening edge is shorter than the length of the side edges, and wherein the opposed side edges and the dent edge of the front body section are joined to those of the back body section, respectively, to form under-crotch cylindrical sections each having the corresponding leg opening at its end, with the lower part of the joined opposed side edges and the joined dent edges. This publication discloses advantages that diapers having such a structure have round-leg cylindrical sections, which may fit on the thighs. Further, the leg openings are spaced apart from the crotch position, so that the leak protection effect may be enhanced. In addition, the design of the diapers closely approximates the design of the trunks-type underwear.

The trunks-type disposable diaper disclosed in Patent Publication 4 has an inner member provided with a stretchable sheet arranged over the inner-thigh-contacting areas and extending continuously in the front-back direction at least from a location crossing the front round-leg elastic members to a location crossing the back round-leg elastic members, the area of the stretchable sheet at least from the location crossing the front round-leg elastic members to the location crossing the back round-leg elastic members is a stretchable area having elongate relay elastic members unintermittently attached along the front-back direction, and at least the stretchable area of the stretchable sheet is joined to the outer member. This publication discloses advantages that, with such a structure, contraction in the width direction of the inner-thigh-contacting areas is prevented to avoid deterioration of the wearing comfort or generation of gaps.

PRIOR ART PUBLICATION

Patent Publication

Patent Publication 1: JP 5717660 B
Patent Publication 2: JP 6323379 B
Patent Publication 3: JP 4912199 B
Patent Publication 4: JP 6752696 B

SUMMARY OF THE INVENTION

Problems to be Solved by the Invention

The disposable diapers disclosed in Patent Publications 1 to 4 above have the elastic members around the legs. For the manufacture of such diapers, for example, elastic members in the form of continuous threads are fed into between a plurality of sheets constituting the outer member, and held and adhered between the sheets. The elastic members, while being fed, are swung for arrangement along the round-leg areas.

However, as the plurality of sheets constituting the outer member travels at a high speed during manufacture, it is not easy to arrange the elastic members along the round-leg areas of the diaper in accordance with the travelling sheets (in particular, positioning is not easy). In fact, the disposable diapers disclosed in Patent Publications 1 to 4 are not easy to manufacture in the context of arrangement of the elastic members.

It is therefore a primary object of the present invention to provide disposable diapers that are easy to manufacture.

Means for Solving the Problem

Typical aspects of the present invention which solve the above problem are as follows.

<First Aspect>

A boxer-shorts-type disposable diaper including:

an outer member having a ventral outer member, a dorsal outer member, and a crotch outer member extending between the ventral outer member and the dorsal outer member and to be placed through a crotch of a wearer, and an inner member containing an absorber body and joined to an interior face of at least the crotch outer member of the outer member, wherein opposed side edges of the ventral outer member and opposed side edges of the dorsal outer member are joined to form a waist opening and a pair of leg openings, wherein the crotch outer member has a pair of inner-thigh-contacting areas extending beyond the absorber body one in one width direction and other in other width direction, and areas extending along edges of the leg openings including the inner-thigh-contacting areas form a pair of leg cylinders each surrounding a groin side of a thigh, wherein the ventral outer member is joined in a middle of a width direction in a crotch-side end to the crotch outer member to form a ventral seam, wherein the dorsal outer member is joined in a middle of a width direction in a crotch-side end to the crotch outer member to form a dorsal seam,

wherein the areas extending along the edges of the leg openings in the ventral outer member and the areas extending along the edges of the leg openings in the dorsal outer member are stretchable in the width direction, and wherein the areas extending along the edges of the leg openings in the crotch outer member are stretchable in a front-back direction.

<Effect>

The general description of the diaper according to the present aspect is that the ventral outer member and the dorsal outer member both stretchable in the width direction are joined to the crotch outer member stretchable in the front-back direction, on the ventral side and the dorsal side, respectively. By dividing the outer member constituting the round-leg areas of the diaper into three members, the ventral outer member, the dorsal outer member, and the crotch outer member, aligning the stretching/contracting direction of the ventral outer member and the dorsal outer member to the width direction and that of the crotch outer member to the front-back direction, and joining these outer members together to compose a diaper, it is no longer required to cause the elastic members to swing along the round-leg areas for arrangement as taught in Patent Publications 1 to 4, facilitating the manufacture.

<Second Aspect>

The boxer-shorts-type disposable diaper according to the first aspect, wherein the ventral seam has a pair of oblique portions extending from opposed right and left sides ventrally with increasing proximity to a middle of the width direction.

<Effect>

With the ventral seam inclined so as to extend from the opposed right and left sides ventrally with increasing proximity to the middle of the width direction, the stretching/contracting directions of the ventral outer member and the stretching/contracting directions of the crotch outer member are neatly connected in a line on the seam, so that the fitting around the legs is enhanced.

<Third Aspect>

The boxer-shorts-type disposable diaper according to the first or second aspect, wherein the dorsal seam has a pair of oblique portions extending from opposed right and left sides dorsally with increasing proximity to a middle of the width direction.

<Effect>

Similarly to the second aspect, with the dorsal seam inclined so as to extend from the opposed right and left sides dorsally with increasing proximity to the middle of the width direction, the stretching/contracting directions of the ventral outer member and the stretching/contracting directions of the crotch outer member are neatly connected in a line on the seam, so that the fitting around the legs is enhanced.

<Fourth Aspect>

The boxer-shorts-type disposable diaper according to the first aspect, wherein the ventral seam has a left oblique portion extending from left side ventrally with increasing proximity to a middle of the width direction, a right oblique portion extending from right side ventrally with increasing proximity to a middle of the width direction, and a connecting portion connecting the left oblique portion and the right oblique portion, and a ventral-most point on the connecting portion of the ventral seam is a ventral connection point, wherein the dorsal seam has a left oblique portion extending from left side dorsally with increasing proximity to a middle of the width direction, a right oblique portion extending from right side ventrally with increasing proximity to a middle of the width direction, and a connecting portion connecting the left oblique portion and the right oblique portion, and a dorsal-most point on the connecting portion of the dorsal seam is a dorsal connection point, and wherein a distance in the front-back direction between a point on the dorsal seam closest to the crotch and the dorsal connection point is shorter than a distance in the front-back direction between a point on the ventral seam closest to the crotch and the ventral connection point.

<Effect>

As the ventral seam and the dorsal seam have a higher rigidity compared to the surroundings, the diaper, when worn, tends to bend gently on the ventral seam and the dorsal seam. As in the present aspect, by rendering the distance in the front-back direction between the point on the dorsal seam closest to the crotch and the dorsal connection point shorter than the distance in the front-back direction between the point on the ventral seam closest to the crotch and the ventral connection point, the area of the dorsal outer member covering the dorsal region when the diaper is worn, may be made larger. As a result, wrapping around the buttocks with the dorsal outer member is facilitated to enhance the wearing comfort of the diaper.

<Fifth Aspect>

The boxer-shorts-type disposable diaper according to the first aspect, wherein the crotch outer member has a left zone and a right zone in the width direction which are stretchable in the front-back direction, and a middle zone in the width direction which is non-stretchable, and wherein the absorber body is joined to the middle zone in the width direction of the crotch outer member.

<Effect>

In the crotch outer member, the middle zone in the width direction, which is joined with the absorber body, is rendered non-stretchable. With such a structure, the absorber body may be kept from being stretched/contracted and distorted under the influence of the outer member stretching/contracting, which avoids deterioration of the wearing comfort and the absorption performance of the diaper.

On the other hand, in the crotch outer member, the left zone and the right zone in the width direction are rendered stretchable in the front-back direction. The left zone and the right zone in the width direction of the crotch outer member are to be brought into close contact with the inner thighs, so that, by rendering these zones stretchable in the front-back direction, the fitting around the legs are enhanced.

<Sixth Aspect>

A method for producing the boxer-shorts-type disposable diapers of the first aspect, including:

joining a separately prepared crotch outer member stretchable in the front-back direction to positions for connecting a crotch-side edge of each region to be the ventral outer member stretchable in the width direction and a crotch-side edge of each region to be the dorsal outer member stretchable in the width direction, to form each integrated outer member wherein the ventral outer member, the crotch outer member, and the dorsal outer member are integrated, joining a separately prepared inner member in its spread state to each integrated outer member to form each inner member-incorporated product, folding each inner member-incorporated product in half in a cross direction to form a folded band product, and joining a ventral outer member to-be and a dorsal outer member to-be of the folded band product along areas corresponding to opposed lateral sides of each diaper to-be, and cutting out the ventral outer member to-be and the dorsal outer member to-be along a border of each diaper to-be, to obtain individual diapers.

<Effect>

For the purpose of imparting the stretching/contracting force to the round-leg areas of the disposable diaper, a separately prepared crotch outer member stretchable in the front-back direction is joined to positions for connecting a crotch-side edge of each region to be the ventral outer member stretchable in the width direction and a crotch-side edge of each region to be the dorsal outer member stretchable in the width direction, to form each integrated outer member wherein the ventral outer member, the crotch outer member, and the dorsal outer member are integrated. With such a structure, it is no longer required to cause the elastic members to swing along the round-leg areas for arrangement as taught in Patent Publications 1 to 4, facilitating manufacture of the diapers.

<Seventh Aspect>

The method for producing the boxer-shorts-type disposable diaper according to the sixth aspect, wherein, in forming the integrated outer member, the ventral outer member to-be is joined in the crotch-side edge to the crotch outer member obliquely to form the ventral seam such that the ventral seam extends from the opposed right and left sides ventrally with increasing proximity to the middle of the width direction.

<Effect>

Effects similar to the ones of the second aspect may be obtained.

<Eighth Aspect>

The method for producing the boxer-shorts-type disposable diaper according to the sixth or seventh aspect, wherein, in forming the integrated outer member, the dorsal outer member to-be is joined in the crotch-side edge to the crotch outer member obliquely to form the dorsal seam such that the dorsal seam extends from the opposed right and left sides dorsally with increasing proximity to the middle of the width direction.

<Effect>

Effects similar to the ones of the third aspect may be obtained.

Effect of the Invention

As discussed above, according to the present invention, disposable diapers are provided that are easy to manufacture.

BRIEF DESCRIPTION OF THE DRAWINGS

FIG. 1 is a plan view (interior face) of the boxer-shorts-type disposable diaper in its spread state.

FIG. 2 is a plan view (exterior face) of the boxer-shorts-type disposable diaper in its spread state.

FIG. 3 is a sectional view taken along lines X-X in FIG. 1.

FIG. 4 is a cross-sectional view taken along lines Y-Y in FIG. 1.

FIG. 5 is a front view seen from the ventral side of the diaper in the as-produced state.

FIG. 6 is a front view seen from the ventral side of the diaper in the worn state.

FIG. 7 is a perspective view of the boxer-shorts-type disposable diaper of FIG. 1 in the worn state, seen obliquely from below in the front.

FIG. 8 is an enlarged view of the crotch absorber body in FIG. 1, with the inner member omitted.

FIG. 9 is a schematic view of the manufacturing process of the boxer-shorts-type disposable diaper according to the present invention.

FIG. 10 is a plan view (interior face) of the boxer-shorts-type disposable diaper in its spread state according to another embodiment.

FIG. 11 is a perspective view of the boxer-shorts-type disposable diaper of FIG. 10 in the worn state, seen obliquely from below in the front.

FIG. 12 is a plan view (interior face) of the boxer-shorts-type disposable diaper in its spread state according to Comparative Example 1.

FIG. 13 is a perspective view (schematic view) of the boxer-shorts-type disposable diaper of FIG. 12 in the worn state, seen obliquely from below in the front.

FIG. 14 is a plan view (interior face) of the boxer-shorts-type disposable diaper in its spread state according to Comparative Example 2.

FIG. 15 is a perspective view (schematic view) of the boxer-shorts-type disposable diaper of FIG. 14 in the worn state, seen obliquely from below in the front.

EMBODIMENTS FOR CARRYING OUT THE INVENTION

An embodiment of the present invention will now be discussed in detail with reference to the attached drawings.

FIGS. 1 to 7 show a boxer-shorts-type disposable diaper 1. This boxer-shorts-type disposable diaper 1 (also referred to simply as diaper 1 hereinbelow) has a waist opening WO and a pair of leg openings LO, and includes an outer member 20 extending from the waist opening edge on the ventral side FS over to the waist opening edge on the dorsal side BS, an inner member 10 containing an absorber body 13 and arranged in at least crotch section C of the outer member 20, and side seals 21 joining the opposed lateral sides in the front and the opposed lateral sides in the back of the outer member 20.

Crotch outer member 20C of the outer member 20 arranged in the crotch section C has a pair of inner-thigh-contacting areas extending beyond the absorber body 13 (in particular, the minimum bounding rectangle of the absorber body 13. The minimum bounding rectangle refers to the virtual rectangle circumscribing the absorber body 13 in the spread state in the plan view and, in the present embodiment, one of the pairs of the opposed sides of the minimum bounding rectangle of the absorber body 13 approximates to the opposed side edges of the inner member 10) in opposed width directions, and areas extending along the edges 29 of the leg openings including the inner-thigh-contacting areas 31 form a pair of leg cylinders 30 each surrounding the groin side of a thigh.

In the manufacture, the inner member 10 is joined to the outer member 20 with joining means, such as a hot melt adhesive, then the inner member 10 and the outer member 20 together are folded along the lateral line passing the center of the front-back direction (longitudinal direction) and forming a border between the front body section F and the back body section, and the opposed lateral sides of the front body section and the opposed lateral sides of the back body section are joined together by means of thermal melt-bonding, a hot melt adhesive, or the like, to form opposed side seals 21, resulting in a boxer-shorts-type disposable diaper 1 having a waist opening WO and a pair of leg openings LO defined therein.

<Example of Inner Member Structure>

The inner member 10 has a structure having, as shown in FIGS. 3 and 4, a liquid-pervious top sheet 11 formed of nonwoven fabric or the like, a liquid-impervious sheet 12 made of polyethylene or the like, and an absorber body 13 interposed therebetween, and absorbs and holds excreted liquid permeating the top sheet 11. The plan shape of the inner member 10 is not particularly limited, and is usually approximately rectangular as shown in FIG. 1 and the like.

<Top Sheet 11>

The top sheet 11 covering the top face side of the absorber body 13 to form a skin-contacting surface may preferably be formed of perforated or non-perforated nonwoven fabric or porous plastic sheet. The raw material fibers constituting the nonwoven fabric may be synthetic fibers, such as polyolefin-based including polyethylene or polypropylene, polyester-based, or polyamide-based fibers, recycled fibers, such as rayon or cupra, or natural fibers, such as cotton, and the nonwoven fabric may have been produced through suitable processing, such as spunlacing, spunbonding, thermal bonding, melt-blowing, or needle punching. Among these processing methods, the spunlacing is superior in imparting flexibility and draping properties, whereas the thermal bonding is superior in imparting bulkiness and softness. With a number of through holes formed through the top sheet 11, urine or the like may rapidly be absorbed, and excellent dry-touch property may be imparted. In the illustrated embodiment, the top sheet 11 is folded around the side edges of the absorber body 13 and extends onto the underside thereof, but is not limited to such an embodiment.

<Liquid-Impervious Sheet 12>

The liquid-impervious sheet 12 covering the underside of the absorber body 13 may be formed of a liquid-impervious sheet of plastic, such as polyethylene or polypropylene, and those having moisture-permeability are preferably used recently for preventing dampness. Such liquid-impervious, moisture-permeable sheet may be a microporous sheet obtained by kneading an inorganic filler in a polyolefin-based resin, such as polyethylene or polypropylene, in a molten state, forming the resulting mixture into a sheet, and then uni- or biaxially drawing the sheet.

As such a liquid-impervious sheet 12, opaque sheet may preferably be used so that the brown color of feces and urine may not be observed through the sheet. Opaqueness may preferably be imparted by internal addition of pigments or fillers, such as calcium carbonate, titanium oxide, zinc oxide, white carbon, clay, talc, or barium sulfate, to a plastic material, which is followed by formation into a film. In the illustrated embodiment, the liquid-impervious sheet 12, together with the top sheet 11, is folded around the side edges of the absorber body 13 and extends onto the underside thereof, but is not limited to such an embodiment.

<Absorber Body 13>

The absorber body 13 may be a commonly-known absorber, for example, an accumulation of pulp fibers, an assembly of filaments, such as of cellulose acetate, or nonwoven fabric, to which a superabsorbent polymer is mixed, fixed, or otherwise, as required. The absorber body 13 may be packaged with a liquid-pervious liquid-retaining packing sheet 14, such as of crepe paper, as required, for retaining its shape and holding the polymer therein. The absorber body 13 and the packing sheet 14 together are referred to as an absorber element 49.

The absorber body 13 as a whole is formed in an approximate shape of an hourglass having a narrowed portion with a shorter width compared to that of the forward and backward portions thereof, in a region extending in the front-back direction and containing the crotch section C, but may be in an otherwise suitable shape, such as a rectangular shape. The dimensions of the narrowed portion may suitably be decided, and the dimension of the narrowed portion in the front-back direction may be about 20 to 50% the overall length of the diaper, and the width of its narrowest part may be about 40 to 60% the overall width of the absorber body 13. When the absorber body has such a narrowed portion, while the plan shape of the inner member 10 is approximately rectangular, the areas of the inner member 10 corresponding to the narrowed portion of the absorber body 13 are left in the absence of the absorber body 13.

<Three-Dimensional Gather Part BG>

On each lateral side of the inner member 10, a three-dimensional gather part BG which fits around the thigh is formed. Each three-dimensional gather part BG has, as shown in FIG. 4, a fixed portion fixed on the under face of the inner member 10 in its lateral portion, a main body portion extending from the fixed portion around the lateral side of the inner member 10 onto the top face of the inner member 10 in its lateral portion, laid-down portions formed by fixing the front and back end portions, respectively, of the main body portion in a laid down state to the top face of the inner member 10 in its lateral portion, and a free portion formed by unfixing the portion between the laid-down portions of the main body portion. These portions are formed from a gathered sheet 22 which has been formed into a duplicate sheet by folding. The gathered sheet 22 may preferably be formed of nonwoven fabric which has been rendered water-repelling.

Between the layers of the duplicate gathered sheet 22, elongate gathering elastic members 16 are arranged in the free edge area or the like of the free portion. The gathering elastic members 16, with their elastic stretching/contracting force, raise the free portion as shown in chain double-dashed lines in FIG. 4 to form each three-dimensional gather part BG in the product state.

Each gathering elastic member 16 may be made of a material that is usually used, for example, polystyrene rubber, polyolefin rubber, polyurethane rubber, polyester rubber, polyurethane, polyethylene, polystyrene, styrene-butadiene copolymer, silicone, or polyester. The gathering elastic members, for making them hardly observable from outside, may preferably have a fineness of 925 dtex or less and are arranged at a tension of 150 to 350% and at intervals of 10.0 mm or less. In addition, the gathering elastic members 16 may be in the form of strings as in the illustrated embodiments, or in the form of tapes having a certain width.

The nonwoven fabric used for the gathered sheet 22 is not particularly limited, and may be composed of synthetic fibers, such as polyolefin-based including polyethylene or polypropylene, polyester-based, or polyamide-based fibers, recycled fibers, such as rayon or cupra, or natural fibers, such as cotton, and may have been produced through suitable processing, such as spunbonding, thermal bonding, melt-blowing, or needle punching. In particular, as the gathered sheet 22, it is preferred to use a water-repellent nonwoven fabric obtained by coating with a silicone, paraffin-metal, or alkyl chromic chloride water repellent for preventing permeation of urea or the like.

<Example of Outer Member Structure>

The outer member 20 may be formed by stacking a plurality of sheets as shown in FIGS. 3 and 4 or by folding one sheet of sheet material. The outer member 20 of the illustrated embodiment has a three-layered structure composed of a presser sheet 7 and a backing sheet 9, each formed of nonwoven fabric or the like, and a stretchable sheet 8 interposed therebetween, which imparts stretchability to the outer member 20. Note that the layered structure of the outer member 20 is not limited to this embodiment and may be, for example, a two-layered structure of the stretchable sheet 8 and the backing sheet 9 without the presser sheet 7, or a two-layered structure of the presser sheet 7 and the stretchable sheet 8 without the backing sheet 9. Further, the outer member 20 may have a single-layer structure of only the stretchable sheet 8 without the presser sheet 7 and the backing sheet 9, or a structure having four or more layers including the presser sheet 7, the stretchable sheet 8, and the backing sheet 9 along with additional sheets.

It should be understood that the stretchable sheet 8 imparts stretching/contracting force in the width direction WD to each of the front body section F and the back body section B, and stretching/contracting force in the front-back direction LD to the crotch section C, to thereby bring the diaper 1 into close contact with the body. The border between waist elastic members 24 and the stretchable sheet 8 may not necessarily be clear. For example, an area may be provided wherein the waist elastic members 24 and the stretchable sheet 8 overlap.

The stretchable sheet 8 has no particular limitation imposed thereon, and may be formed of an elastic film, such as a thermoplastic resin sheet having elasticity in itself or stretchable nonwoven fabric. Use of stretchable nonwoven fabric hardly causes creases on the diaper surface, which may make the appearance of the diaper closer to that of underwear, and may avoid drawbacks like emergence of diaper creases on outerwear like trousers. The stretchable sheet 8 may have no perforations or may have a multitude of perforations or slits formed therein for air permeation. The stretchable sheet 8 is particularly preferably an elastic sheet having a tensile strength in the width direction WD (stretching/contracting direction ED, machine direction MD) of 8 to 25 N/35 mm, a tensile strength in the front-back direction LD (direction orthogonal to the stretching/contracting direction XD, cross direction CD) of 5 to 20 N/35 mm, a tensile elongation in the width direction WD of 450 to 1050%, and a tensile elongation in the front-back direction LD of 450 to 1400%. The thickness of the stretchable sheet 8 is not particularly limited, and may preferably be about 20 to 40 μm. Further, the stretchable sheet 8 may be nonwoven sheet having a structure with two or a plurality of layers. Such a nonwoven sheet has elongate elastic members interposed between arbitrary sheets constituting the nonwoven sheet, and the stretching/contracting action of the elongate elastic members makes the overall nonwoven sheet stretchable/contractible. It should be understood that, with the stretchable sheet 8 having the elongate elastic members interposed therein, it is preferred to arrange a folded portion or the like exterior to the stretchable sheet 8 so that creases or the like will not appear on the external face upon contraction.

The stretchability may alternatively be imparted to the outer member 20 by providing elastic members, rather than the stretchable sheet 8. For example, the outer member 20 may be provided with a various types of elastic members for imparting stretchability. In this case, a plurality of sheet layers is provided at least in the area containing the elastic members, which are interposed between the sheet layers. Such a plurality of sheet layers may be formed of a single sheet of a sheet material for each layer, or by folding a single sheet of a sheet material. Specifically, the outer member 20 may be formed in a two-layered structure of the presser sheet 7 and the backing sheet 9, each formed of nonwoven fabric, and stretchability is imparted thereto by arranging various types of elastic members 24 or the like between the presser sheet 7 and the backing sheet 9, and between doubled nonwoven fabric in folded portion 20D formed by folding the backing sheet 9 along the waist opening edge onto the interior face.

The outer member 20 may be composed, for example, of a ventral outer member 20F arranged on the ventral side FS of the front-back direction LD, a dorsal outer member 20B arranged on the dorsal side BS of the front-back direction LD, and a crotch outer member 20C arranged in the crotch section C located therebetween. The dimension in the width direction WD of the crotch outer member 20C is shorter than the dimensions in the width direction WD of the ventral outer member 20F and the dorsal outer member 20B, resulting in the outer member 20 having its middle portion in the front-back direction LD narrowed in shape. It should be understood that the dorsal edges in the front-back direction LD of the ventral outer member 20F, the ventral edges in the front-back direction LD of the dorsal outer member 20B, and the opposed lateral edges of the crotch outer member 20C together form the edges 29 of the leg openings.

<Segmented Structure of Outer Member 20>

The outer member 20 is segmented into the ventral outer member 20F, the dorsal outer member 20B, and the crotch outer member 20C extending between the ventral outer member 20F and the dorsal outer member 20B to be placed through the crotch of the wearer. The ventral outer member 20F is joined in the middle of the width direction in the crotch-side end to the crotch outer member 20C to form a ventral seam 90F. The dorsal outer member 20B is joined in the middle of the width direction in the crotch-side end to the crotch outer member 20C to form a dorsal seam 90B. The areas extending along the edges of the leg openings in the ventral outer member 20F and the areas extending along the edges of the leg openings in the dorsal outer member 20B are stretchable in the width direction WD, while the areas extending along the edges of the leg openings in the crotch outer member 20C are stretchable in the front-back direction LD. In this way, segmenting the outer member 20, which forms the round-leg areas of the diaper 1, into three sections, i.e., the ventral outer member 20F, the dorsal outer member 20B, and the crotch outer member 20C, joining the three to form the seams 90, and aligning the stretching/contracting directions of the ventral outer member 20F and the dorsal outer member 20B to the width direction WD and aligning the stretching/contracting direction of the crotch outer member 20C to the front-back direction LD, eliminate the necessity to cause the elastic members to swing for arrangement along the round-leg areas as in the inventions disclosed in the prior art patent publications discussed above, facilitating the manufacture.

<Seam 90>

As shown in FIG. 8, the ventral seam 90F of the seams 90 preferably extends obliquely from the opposed right and left sides ventrally FS with increasing proximity to the middle of the width direction WD. With the ventral seam 90F having oblique portions 90FL, 90FR, the stretching/contracting direction ECF of the ventral outer member 20F and the stretching/contracting direction ECC of the crotch outer member 20C may be connected neatly in a line on the seam portions 90FL, 90FR, so that the fitting around the legs is enhanced.

Similarly, dorsal seam 90B of the seams 90 preferably extends obliquely from the opposed right and left sides dorsally BS with increasing proximity to the middle of the width direction WD. In this way, with the dorsal seam 90B having oblique portions 90BL, 90BR, the stretching/contracting direction ECB of the dorsal outer member 20B and the stretching/contracting direction ECC of the crotch outer member 20C may be connected neatly in a line on the seam portions 90BL, 90BR, so that the fitting around the legs is enhanced.

The inclination angles A1 to A4 of the ventral seam 90F and the dorsal seam 90B may arbitrarily be decided, and may be preferably about 5 to 45 degrees, more preferably about 10 to 30 degrees. At an inclination angle of less than 5 degrees or over 45 degrees, the stretching/contracting directions in the round-leg areas of the ventral outer member 20F (crotch-side areas), the round-leg areas of the dorsal outer member 20B (crotch-side areas), and the round-leg areas of the crotch outer member 20C (opposed sides in the width direction WD) may be hard to be connected neatly in a line, so that the fitting around the legs may be inferior.

Note that the inclination angle A1 of the ventral seam 90F on its left side LS in the width direction WD refers to the angle (interior angle) between ventral virtual line FLF, which connects with a straight line the starting point 91FL of the left oblique portion 90FL and the starting point of the right oblique portion 90FR of the ventral seam 90F, and the left oblique portion 90FL of the ventral seam 90F. No particular question may arise when the left oblique portion 90FL of the ventral seam 90F is formed in a straight line, but the left oblique portion 90FL of the ventral seam 90F may be formed in a curved line as shown in FIG. 8. For such a curved line, a tangent line to the left oblique portion 90FL of the ventral seam 90F is drawn at the starting point 91FL of the left oblique portion 90FL of the ventral seam 90F (referred to as a virtual tangent line TL1), and the angle between this virtual tangent line TL1 and the ventral virtual line FLF is defined as the inclination angle A1. Similarly, for the inclination angle A2 of the ventral seam 90F on its right side RS in the width direction WD, as shown in FIG. 8, a tangent line to the right oblique portion 90FR of the ventral seam 90F is drawn at the starting point 91FR of the right oblique portion 90FR of the ventral seam 90F (referred to as a virtual tangent line TL2), and the angle (interior angle) between this virtual tangent line TL2 and the ventral virtual line FLF is defined as the inclination angle A2.

The same applies to the dorsal seam 90B. Specifically, the inclination angle A3 of the dorsal seam 90B on its left side LS in the width direction WD refers to the angle (interior angle) between dorsal virtual line FLB, which connects with a straight line the starting point 91BL of the left oblique portion 90BL and the starting point of the right oblique portion 90BR of the dorsal seam 90B, and the left oblique portion 90BL of the dorsal seam 90B. When the left oblique portion 90BL of the dorsal seam 90B is formed in a curved line as shown in FIG. 8, a tangent line to the left oblique portion 90BL of the dorsal seam 90B is drawn at the starting point 91BL of the left oblique portion 90BL of the dorsal seam 90B (referred to as a virtual tangent line TL3), and the angle between this virtual tangent line TL3 and the dorsal virtual line FLB is defined as the inclination angle A3. Similarly, for the inclination angle A4 of the dorsal seam 90B on its right side RS in the with direction WD, as shown in FIG. 8, a tangent line to the right oblique portion 90BR of the dorsal seam 90B is drawn at the starting point 91BR of the right oblique portion 90BR of the dorsal seam 90B (referred to as a virtual tangent line TL4), and the angle (interior angle) between this virtual tangent line TL4 and the dorsal virtual line FLB is defined as the inclination angle A4.

As shown in FIG. 8, the ventral seam 90F preferably has the left oblique portion 90FL extending from the left side LS ventrally FS with increasing proximity to the middle of the width direction WD, the right oblique portion 90FR extending from the right side RS ventrally FS with increasing proximity to the middle of the width direction WD, and a connecting portion 90FT connecting the left oblique portion 90FL and the right oblique portion 90FR. Similarly, the dorsal seam 90B also preferably has the left oblique portion 90BL extending from the left side LS dorsally BS with increasing proximity to the middle of the width direction WD, the right oblique portion 90BR extending from the right side RS dorsally BS with increasing proximity to the middle of the width direction WD, and a connecting portion 90BT connecting the left oblique portion 90BL and the right oblique portion 90BR.

Referring to the ventral-most FS point on the connecting portion 90FT of the ventral seam 90F as a ventral connection point 91FT and referring to the dorsal-most BS point on the connecting portion 90BT of the dorsal seam 90B as a dorsal connection point 91BT, it is preferred that the distance BL in the front back direction LD between the point 91BL/91BR on the dorsal seam 90B located closest to the crotch (in the embodiment of FIG. 8, 91BL and 91BR are located at the same level in the front-back direction LD) and the dorsal connection point 91BT is rendered shorter than the distance FL in the front-back direction LD between the point 91FL/91FR on the ventral seam 90F located closest to the crotch (in the embodiment of FIG. 8, 91FL and 91FR are located at the same level in the front-back direction LD) and the ventral connection point 91FT. With such an arrangement, the area of the dorsal outer member 20B covering the buttocks when the diaper is worn is larger, which facilitates wrapping around the buttocks with the dorsal outer member 20B to enhance the wearing comfort of the diaper. The distance BL in the front-back direction LD is preferably 5 to 50 mm, more preferably 10 to 40 mm, from the point on the dorsal seam 90B closest to the crotch (where the points 91BL and 91BR are located at the same level in the front-back direction LD, the point 91BL and the point 91BR, and where the points 91BL and 91BR are located at different levels in the front-back direction LD, the point closer to the crotch (91BL or 91BR), as the case may be) to the dorsal connection point 91BT. The distance FL in the front-back direction LD is preferably 10 to 60 mm, more preferably 15 to 50 mm, from the point on the ventral seam 90F closest to the crotch (where the points 91FL and 91FR are located at the same level in the front-back direction LD, the point 91FL and the point 91FR, and where the points 91FL and 91FR are located at different levels in the front-back direction LD, the point closer to the crotch (91FL or 91FR), as the case may be) to the ventral connection point 91FT. The difference is preferably 5 to 30 mm, more preferably 10 to 20 mm, between the distance BL in the front-back direction LD between the point on the dorsal seam 90B closest to the crotch and the dorsal connection point 91BT and the distance FL in the front-back direction LD between the point on the ventral seam 90F closest to the crotch and the ventral connection point 91FT.

It should be understood that the connecting portion 90FT is provided in the ventral seam 90F in the embodiment shown in FIGS. 1 and 8, but may not necessarily be provided. This is because the absorber body 13 is often joined to the connecting portion 90FT, and the portion of the outer member 20 to which the absorber body 13 is joined is often made non-stretchable, so that the effects, such as the neat connection of the stretching/contracting direction ECF of the ventral outer member 20F and the stretching/contracting direction ECC of the crotch outer member 20C in a line to enhance the fitting around the legs, may hardly be obtained. In the dorsal seam 90B, the connecting portion 90BT may not necessarily be provided, for the similar reason as for the ventral seam 90F.

As shown in FIGS. 6 and 7, the seams 90 are formed by joining with a hot melt adhesive or the like, and thus often have a higher rigidity compared to the areas around the seams 90. Consequently, when the diaper 1 is worn, the outer member 20 is bent along the seams 90 to form a diaper 1 with depth in the crotch section, like boxer-shorts-type underwear.

<Inner-Thigh-Contacting Area 31>

The crotch outer member 20C of the outer member 20 has a pair of inner-thigh-contacting areas 31 extending beyond the absorber body 13 (in particular, the minimum bounding rectangle of the absorber body 13) in opposed width directions WD, and areas extending along the edges 29 of the leg openings 29 including the inner-thigh-contacting areas 31 form a pair of leg cylinders 30 each surrounding the groin side of a thigh. The width of each inner-thigh-contacting area 31 (distance in the width direction WD between a side edge of the absorber body 13 and the corresponding side edge of the crotch outer member 20C) is preferably 10 to 80 mm, more preferably 20 to 60 mm. Further, this width of each inner-thigh-contacting area 31 is preferably 5 to 40%, more preferably 10 to 30% the overall width of the crotch outer member 20C.

<Stretchability and Non-stretchability of Crotch Outer Member 20C>

In the crotch outer member 20C, it is preferred that the left side zone in the width direction WD and the right side zone in the width direction WD are made stretchable in the front-back direction, while the middle zone in the width direction WD is made non-stretchable. Then, it is preferred to join the absorber body 13 to the middle zone in the width direction WD, which is the non-stretchable area, of the crotch outer member 20C. With such an arrangement, the absorber body 13 may be kept from stretching/contracting and being distorted under the influence of the stretching/contracting of the crotch outer member 20C, which avoids deterioration of the wearing comfort and absorption performance of the diaper 1. Further, as the left side zone in the width direction WD and the right side zone in the width direction WD of the crotch outer member 20C will be brought into close contact with the inner thighs, stretching/contracting of these zones in the front-back direction LD may enhance the fitting around the legs. Note that the left side zone in the width direction WD and the right side zone in the width direction WD of the crotch outer member 20C correspond to the inner-thigh-contacting areas 31.

In the embodiment of FIG. 2, in the crotch outer member 20C, the ventral outer member 20F, and the dorsal outer member 20B, the entire region coincident with the absorber body 13 is made non-stretchable (referred to as the non-stretchable region 19), while the remaining region is made stretchable. However, the present invention is not limited to this embodiment and, for example, part of the region coincident with the absorber body 13 may be made the non-stretchable region 19, while the remaining region may be made the stretchable region. Alternatively, the non-stretchable region 19 may be provided not only in the region coincident with the absorber body 13, but also in part of the region not coincident with the absorber body 13. For example, the entire region coincident with the inner member 10 may be made the non-stretchable region 19.

<Joining of Outer Member 20 and Inner Member 10>

FIG. 2 shows a zone wherein the inner member 10 is joined to the outer member 20 (inner member-joined zone 18) in gray. In the embodiment of FIG. 2, the overall under face of the inner member 10 is joined to the outer member 20, but the present invention is not limited to this embodiment, and only a part of the under face of the inner member 10 may be joined to the outer member 20.

<Waist Elastic Member 24>

The waist elastic members 24 are in the form of a plurality of elongate elastic members, such as rubber threads, arranged at intervals in the front-back direction in the vicinity of the waist opening within the extent in the front-back direction of the side seals 21 joining the front body section F and the back body section B, and constrict around the body in the vicinity of the waist opening of the diaper for fitting the diaper. The waist elastic members 24, which are a plurality of rubber threads in the illustrated embodiment, may instead be, for example, a stretchable member in the form of a tape. Further, the waist elastic members 24, which are held in the folded portion 20D of the backing sheet 9 between the doubled nonwoven fabric in the waist zone in the illustrated embodiment, may be held between the presser sheet 7 and the backing sheet 9. The stretch rates of the elastic members 24 in the fixed state may suitably be decided, and may be about 160 to 320% for ordinary adult diapers.

<Front/Back Presser Sheets 50, 51>

As shown in FIG. 3, front/back presser sheets 50, 51 may be provided for covering the front and back end areas of the inner member 10 attached to the interior face of the outer member 20, and for preventing leakage through the front and back edges of the inner member 10. Discussing the illustrated embodiment in further detail, the front presser sheet 50 extends over the entire width on the interior face of the front body section F from the interior face of the folded portion 20D onto the front end area of the inner member 10, whereas the back presser sheet 51 extends over the entire width on the interior face of the back body section B from the interior face of the folded portion 20D onto the back end area of the inner member 10. The front/back presser sheets 50, 51 separately formed and attached as in the illustrated embodiment advantageously provide a higher degree of freedom in material choice, but disadvantageously increase the amount of material required or the manufacturing processes. In view of this, the folded portion 20D may be extended to partly overlap the inner member 10 to thereby form a portion equivalent to the presser sheets 50, 51 discussed above.

<Method of Manufacture>

FIG. 9 illustrates an embodiment of the method for producing the boxer-shorts-type disposable diapers according to the present invention. In the figure, FIG. 9(*a*) shows the main line, FIGS. 9(*b*) and 9(*c*) show sub-lines, MD refers to the machine direction (flow direction of the line), and CD refers to the cross machine direction (direction orthogonal to the flow direction of the line).

FIG. 9 illustrates not the entire process of manufacturing the diapers, but mainly the assembly of the inner member 10 and the outer member 20, including the steps before and after the assembly, extracted from the process, and shows the process of gradual completion of a diaper from left to right of the figure. For the sake of clarity, method for producing diapers having rubber threads (elastic members) arranged almost over the surface of the outer member 20 (except for the areas to which the inner member 10 is to be attached) is illustrated, but diapers having a stretchable film or stretchable nonwoven fabric, instead of the rubber threads, arranged almost over the surface of the outer member 20 may also be manufactured in the similar way.

In the main line shown in FIG. 9(*a*), the regions to be the ventral outer members 20F and the regions to be the dorsal outer members 20B are conveyed in the MD, with the width direction WD of these outer members 20F, 20B aligned to the MD. In the sub-line shown in FIG. 9(*b*), the regions to be the crotch outer members 20C are conveyed in the MD, with the front-back direction LD of the crotch outer members 20C aligned to the MD. In the sub-line shown in FIG. 9(*c*), the regions to be the inner members 10 are conveyed in the MD, with the front-back direction LD of the inner member 10 aligned to the MD.

In the sub-line in FIG. 9(*b*), individual crotch outer members 20C are cut out, and then turned 90 degrees. Similarly, in the sub-line in FIG. 9(*c*), individual inner members 10 are cut out, and then turned 90 degrees.

On the other hand, in the main line in FIG. 9(*a*), each region to be the ventral outer member 20F and each region to be the dorsal outer member 20B are cut (CT) in the middle of the width direction WD in their crotch-side edges in a rounded pattern. Then over the cut-away areas, a crotch outer member 20C manufactured in the sub-line in FIG. 9(*b*) is mounted, the ventral outer member 20F and the crotch outer member 20C are joined and the dorsal outer member 20B and the crotch out member 20C are joined, each along the edge of the corresponding rounded cut, to thereby form an integrated outer member 70 having the outer members 20F, 20C, 20B integrated (wherein the rounded seams are referred to as the ventral seam 90F and the dorsal seam 90B) (the process for producing this integrated outer member 70 is referred to as the integrated outer member-producing step). Then, on the integrated outer member 70, an inner member 10 manufactured in the sub-line in FIG. 9(*c*) is mounted and joined thereto to form an inner member-incorporated product (the process for producing this inner member-incorporated product is referred to as the inner member-incorporating step). Next, the inner member-incorporated product 71 is folded in half in the CD along the lateral line CL passing the center of the front-back direction LD to form a folded band product 72 (the process for producing this folded band product 72 is referred to as the folding step). Finally, the ventral outer member 20F to-be and the dorsal outer member 20B to-be are joined along the areas corresponding to the opposed lateral sides of each diaper (forming side seals 21), and then the ventral outer member 20F to-be and the dorsal outer member 20B to-be are cut out along the border of each diaper to-be to thereby obtain individual diapers 1 (the process of joining the opposed lateral sides and cutting along the border is referred to as the lateral joining/separating step).

It should be understood that in the main line of FIG. 9(*a*), the step of cutting (CT) each region to be the ventral outer member 20F and each region to be the dorsal outer member 20B in the middle of the width direction WD in their crotch-side edges in a rounded pattern may be omitted. In this case, diapers 1 each having a rounded ventral seam 90F and a rounded dorsal seam 90B may be obtained by rounding the shape of each seam in joining the ventral outer member 20F and the crotch outer member 20C and joining the dorsal outer member 20B and the crotch outer member 20C. By omitting the step of cutting (CT) in a rounded pattern, the manufacturing process is simplified and the manufacturing speed may be increased, while the wastes generated by the cutting (CT) may advantageously be eliminated.

Further, in the embodiment discussed above, the shapes of the seams are rounded, but it is not always necessary to round the seams, and modification to any arbitrary shapes, such as straight lines extending ventrally FS (or dorsally BS) toward the middle of the width direction WD, is encompassed.

As discussed above, joining the crotch outer member 20C stretchable in the front-back direction LD to the ventral outer member 20F and the dorsal outer member 20B, both stretchable in the width direction WD, to thereby obtain a diaper 1, eliminates the necessity to cause the elastic members to swing for arrangement along the round-leg areas as taught in Patent Publications 1 to 4 discussed above, which facilitates the manufacture.

<Before Wearing and After Wearing>

The boxer-shorts-type disposable diaper 1 before it is worn (in the product state) is shown in FIG. 5, whereas the boxer-shorts-type disposable diaper 1 when it is worn is shown in FIG. 6. Before worn, the diaper is configured with the crotch outer member 20C projecting toward the crotch side CS in the front-back direction LD, whereas when worn, the diaper attains the depth, and the crotch outer member 20C is brought into contact with the crotch of the wearer to extend from the ventral side over to the dorsal side, which makes the crotch outer member 20C hardly observable when the diaper 1 is seen from the front. Further, the opposed lateral sides in the width direction WD of the crotch outer member 20C (in particular, the inner-thigh-contacting areas 31) are pressed down by the legs of the wearer of the diaper 1 to form a pair of round-thigh opening areas. FIG. 6 shows that the pair of round-thigh opening areas thus formed has just a one-tenth length. It is indisputable that the present invention is not limited to the one-tenth length, and may be in two-tenth length or longer.

Other Embodiments

FIGS. 1, 2 and the like show the diaper 1 of which lower-torso region (regions of the front body section F and the back body section B exclusive of the vicinity of the waist opening WO) and the crotch section C are composed of stretchable film or stretchable nonwoven fabric. Use of such stretchable film or stretchable nonwoven fabric hardly causes creases on the diaper surface compared to the rubber threads or the like, which may make the appearance of the diaper closer to that of boxer-shorts-type underwear, and thus drive the consumers who are looking for diapers having an underwear-like appearance, to buy the product.

The present invention is not limited to such an embodiment. For example, as shown in FIG. 10, an embodiment having elastic members 25, 26, 27 in the form of rubber threads or the like, arranged in the lower torso section and/or crotch section C may be conceivable. Generally, elastic members 25, 26, 27 produce stronger constriction force compared to the stretchable film or the stretchable nonwoven fabric, so that use of the elastic members 25, 26, 27 may enhance the fitting of the diaper compared to the use of the stretchable film or the stretchable nonwoven fabric. In the embodiment of FIG. 10, the middle zone in the front-back direction (the zone exclusive of the opposed end portions in the front-back direction LD) of each of the front body section F and the back body section B is provided with lower-torso elastic members 25, the crotch-side area in the front-back direction LD of each of the front body section F and the back body section B is provided with round-leg elastic members 26, and the crotch section C is provided with crotch elastic members 27.

It is seen that the round-leg elastic members 26 and the crotch elastic members 27 meet generally at the oblique portions of the seams 90, where the stretching/contracting directions of the ventral outer member 20F and the dorsal outer member 20B (stretching/contracting in the width direction WD) are neatly connected in a line with the stretching/contracting direction of the crotch outer member 20C (stretching/contracting in the front-back direction LD). In this way, by connecting the stretching/contracting directions of the outer member 20 in a line so as to surround the legs of the wearer, the fitting around the legs may be enhanced.

It should be understood that the lower-torso elastic members 25 and the round-leg elastic members 26 are each in the form of a plurality of elongate elastic members, such as rubber threads, arranged at intervals in the front-back direction, like the waist elastic members 24. The crotch elastic members 27 are in the form of a plurality of elongate elastic members, such as rubber threads, arranged at intervals in the width direction WD. The elastic members 25, 26, 27 in the illustrated embodiment are in the form of a plurality of rubber threads, which may be replaced with, for example, stretchable members in the form of tapes. Further, the elastic members 25, 26, 27 may be positioned anywhere without particular limitations, and may be, for example, held between the presser sheet 7 and the backing sheet 9. The stretch rates of the elastic members 25, 26, 27 in the fixed state may suitably be decided, and may be about 160 to 320% for ordinary adult diapers.

FIG. 11 shows the diaper 1 according to another embodiment of FIG. 10 in the worn state. In FIG. 11, for the sake of legibility of the figure, illustration of the lower-torso elastic members 25 is omitted (actually present), while the waist elastic members 24, the round-leg elastic members 26, and the crotch elastic members 27 are illustrated. As may be seen from this figure, the round-leg elastic members 26 and the crotch elastic members 27 are neatly connected to surround the legs of the wearer, resulting in enhanced fitting around the legs.

FIGS. 12 and 13 show a diaper 1 of Comparative Example 1. Note that in FIG. 13, too, for the sake of legibility of the figure, illustration of the lower-torso elastic members 25 is omitted (actually present), while the waist elastic members 24, the round-leg elastic members 26, and the crotch elastic members 27 are illustrated.

In the example of Comparative Example 1, each of the ventral seam 90F and the dorsal seam 90 B is formed in a straight line in the width direction WD. In the embodiment of FIGS. 10 and 11, the ventral seam 90F protrudes ventrally FS (convex shape), and the dorsal seam 90 B protrudes dorsally (convex shape), whereas in the example of Comparative Example 1, no such protrusion is present.

With the example of Comparative Example 1, as may be seen clearly from FIG. 13, the round-leg elastic members 26 and the crotch elastic members 27 are not connected neatly on the seams 90, not surrounding the legs of the wearer. Specifically, as portions of the round-leg elastic members 26 closer to the middle of the width direction WD extend as far as to the inner member 10, the contraction force in the width direction WD becomes intense, causing the diaper to tense in the width direction WD. This results in the disadvantage of hardly enhanceable fitting around the legs.

FIGS. 14 and 15 show a diaper of Comparative Example 2. Note that in FIG. 15, too, for the sake of legibility of the figure, illustration of the lower-torso elastic members 25 is omitted (actually present), while the waist elastic members 24, the round-leg elastic members 26, and the crotch elastic members 27 are illustrated.

In the example of Comparative Example 2, the ventral seam 90F protrudes ventrally FS (convex shape), and the dorsal seam 90B protrudes dorsally BS (convex shape). However, the protruding shapes are different from those in FIG. 1 or the like. Specifically, the ventral seam 90F and the dorsal seam 90B in FIG. 1 or the like have the oblique portions as discussed above, whereas the example of Comparative Example 2 has no such oblique portion. In other words, each of the interior angles A1 to A4 discussed above is 90 degrees.

With the example of Comparative Example 2, as may be seen clearly from FIG. 15, the round-leg elastic members 26 and the crotch elastic members 27 are not connected neatly on the seams 90, not surrounding the legs of the wearer. Specifically, the front end portions in the front-back direction LD of the crotch elastic members 27 extend ventrally FS for a longer extent, and the back end portions in the front-back direction LD of the crotch elastic members 28 extend dorsally BS for a longer extent, so that the overall contracting force in the front-back direction LD becomes stronger, causing the diaper to tense in the front-back direction LD. This results in the disadvantage of hardly enhanceable fitting around the legs.

For avoiding such disadvantages, the ventral seam 90F and the dorsal seam 90B are preferably provided with the oblique portions 90FL, 90FR, 90BL, 90BR on the left side FS and the right side RS in the width direction WD. It should be understood that the oblique portions 90FL, 90FR, 90BL, 90BR are not necessarily in the curved shapes as shown in FIG. 8, and may be in arbitrary shapes, such as a straight line.

In Comparative Examples 1 and 2 above, discussions have been made with reference to the examples having the round-leg elastic members 26 and the crotch elastic members 27, which are not limiting. That is, the same applies even when the round-leg elastic members 26 and the crotch elastic members 27 are replaced with stretchable film or stretchable nonwoven fabric.

The perspective views in FIGS. 7, 11, 13, and 15 show only the front body section F and the crotch section C, but the back body section B is in the similar state.

Accordingly, as discussed above, it is also preferred to provide the dorsal seam 90B in the back body section B with the oblique portions 90BL, 90BR.

<Explanation of Terms in the Specification>

The following terms appearing in the present specification shall have the following means unless otherwise specified herein.

The "stretch rate" refers to a value with respect to the natural length being 100%.

The "spread state" refers to the state in which a diaper is spread flatly without contraction or slack.

The sizes and positional relationships of various parts refer to those not in the natural length state but in the spread state, unless otherwise specified.

INDUSTRIAL APPLICABILITY

The present invention is applicable to boxer-shorts-type disposable diapers, such as those discussed above.

DESCRIPTION OF REFERENCE SIGNS

1: boxer-shorts-type disposable diaper
7: presser sheet

8: stretchable sheet
9: backing sheet
10: inner member
11: top sheet
12: liquid impervious sheet
13: absorber body
14: packing sheet
16: gathering elastic members
18: inner member-joined zone
19: non-stretchable region
20: outer member
20F: ventral outer member
20C: crotch outer member
20B: dorsal outer member
20D: folded portion
21: side seal
22: gathered sheet
24: waist elastic member
25: lower-torso elastic member
26: round-leg elastic member
27: crotch elastic member
29: edge of leg opening
30: leg cylinder
31: inner-thigh-contacting area
49: absorber element
50: front presser sheet
51: back presser sheet
70: integrated outer member
71: inner member-incorporated product
72: doubled band product
90: seam
90F: ventral seam
90B: dorsal seam
BG: three-dimensional gather part
F: front body section
C: crotch section
B: back body section
LD: front-back direction
FS: ventral side (front side)
BS: dorsal side (back side)
WD: width direction
LS: left side
RS: right side
TD: thickness direction
INS: inside
OUS: outside

The invention claimed is:

1. A boxer-shorts-type disposable diaper comprising:

an outer member having a ventral outer member, a dorsal outer member, and a crotch outer member extending between the ventral outer member and the dorsal outer member and to be placed through a crotch of a wearer, and an inner member containing an absorber body and joined to an interior face of at least the crotch outer member of the outer member, wherein opposed side edges of the ventral outer member and opposed side edges of the dorsal outer member are joined to form a waist opening and a pair of leg openings, wherein the crotch outer member has a pair of inner-thigh-contacting areas extending beyond the absorber body one in one width direction and other in other width direction, and areas extending along edges of the leg openings including the inner-thigh-contacting areas form a pair of leg cylinders each configured to be positioned adjacent to a groin side of a thigh, wherein the ventral outer member is joined in a middle of a width direction in a crotch-side end to the crotch outer member to form a ventral seam, wherein the dorsal outer member is joined in a middle of a width direction in a crotch-side end to the crotch outer member to form a dorsal seam, wherein the areas extending along the edges of the leg openings in the ventral outer member and the areas extending along the edges of the leg openings in the dorsal outer member are stretchable in the width direction, wherein the areas extending along the edges of the leg openings in the crotch outer member are stretchable in a front-back direction, wherein the ventral seam has a left oblique portion extending from left side ventrally with increasing proximity to a middle of the width direction, a right oblique portion extending from right side ventrally with increasing proximity to a middle of the width direction, and a connecting portion connecting the left oblique portion and the right oblique portion, and a ventral-most point on the connecting portion of the ventral seam is a ventral connection point, wherein the dorsal seam has a left oblique portion extending from left side dorsally with increasing proximity to a middle of the width direction, a right oblique portion extending from right side dorsally with increasing proximity to a middle of the width direction, and a connecting portion connecting the left oblique portion and the right oblique portion, and a dorsal-most point on the connecting portion of the dorsal seam is a dorsal connection point, and wherein a distance in the front-back direction between a point on the dorsal seam closest to the crotch and the dorsal connection point is shorter than a distance in the front-back direction between a point on the ventral seam closest to the crotch and the ventral connection point.

2. A method for producing boxer-shorts-type disposable diapers, wherein each boxer-shorts-type disposable diaper comprises:

an outer member having a ventral outer member, a dorsal outer member, and a crotch outer member extending between the ventral outer member and the dorsal outer member and to be placed through a crotch of a wearer, and an inner member containing an absorber body and joined to an interior face of at least the crotch outer member of the outer member, wherein opposed side edges of the ventral outer member and opposed side edges of the dorsal outer member are joined to form a waist opening and a pair of leg openings, wherein the crotch outer member has a pair of inner-thigh-contacting areas extending beyond the absorber body one in one width direction and other in other width direction, and areas extending along edges of the leg openings including the inner-thigh-contacting areas form a pair of leg cylinders each configured to be positioned adjacent to a groin side of a thigh, wherein the ventral outer member is joined in a middle of a width direction in a crotch-side end to the crotch outer member to form a ventral seam, wherein the dorsal outer member is joined in a middle of a width direction in a crotch-side end to the crotch outer member to form a dorsal seam, wherein the areas extending along the edges of the leg openings in the ventral outer member and the areas extending along the edges of the leg openings in the dorsal outer member are stretchable in the width direction, wherein the areas extending along the edges of the leg openings in the crotch outer member are stretchable in a front-back direction, and wherein the method comprises:

joining a separately prepared crotch outer member stretchable in the front-back direction to positions for connecting a crotch-side edge of each region to be the ventral outer member stretchable in the width direction and a crotch-side edge of each region to be the dorsal outer member stretchable in the width direction, to form each integrated outer member wherein the ventral outer member, the crotch outer member, and the dorsal outer member are integrated, joining a separately prepared inner member in its spread state to each integrated outer member to form each inner member-incorporated product, folding each inner member-incorporated product in half in a cross direction to form a folded band product, and joining a ventral outer member to-be and a dorsal outer member to-be of the folded band product along areas corresponding to opposed lateral sides of each diaper to-be, and cutting out the ventral outer member to-be and the dorsal outer member to-be along a border of each diaper to-be, to obtain individual diapers.

3. The method for producing the boxer-shorts-type disposable diaper according to claim 2, wherein, in forming the integrated outer member, the ventral outer member to-be is joined in the crotch-side edge to the crotch outer member obliquely to form the ventral seam such that the ventral seam extends from the opposed right and left sides ventrally with increasing proximity to the middle of the width direction.

4. The method for producing the boxer-shorts-type disposable diaper according to claim 3, wherein, in forming the integrated outer member, the dorsal outer member to-be is joined in the crotch-side edge to the crotch outer member obliquely to form the dorsal seam such that the dorsal seam extends from the opposed right and left sides dorsally with increasing proximity to the middle of the width direction.

5. The method for producing the boxer-shorts-type disposable diaper according to claim 2, wherein, in forming the integrated outer member, the dorsal outer member to-be is joined in the crotch-side edge to the crotch outer member obliquely to form the dorsal seam such that the dorsal seam extends from the opposed right and left sides dorsally with increasing proximity to the middle of the width direction.

* * * * *